United States Patent [19]

Jadhav et al.

[11] Patent Number: 5,506,355
[45] Date of Patent: Apr. 9, 1996

[54] METHOD FOR PREPARING CYCLIC SULFAMIDES AND THEIR USE FOR THE SYNTHESIS OF HIV PROTEASE INHIBITORS

[75] Inventors: Prabhakar K. Jadhav, Wilmington, Del.; Wayne F. Daneker, West Grove, Pa.; Francis J. Woerner, Bear, Del.

[73] Assignee: The Du Pont Merck Pharmaceutical Company, Wilmington, Del.

[21] Appl. No.: 269,281

[22] Filed: Jun. 30, 1994

Related U.S. Application Data

[63] Continuation-in-part of Ser. No. 197,630, Feb. 16, 1994, which is a continuation-in-part of Ser. No. 47,330, Apr. 15, 1993, abandoned, which is a continuation-in-part of Ser. No. 23,439, Feb. 26, 1993, abandoned.

[51] Int. Cl.$^6$ ............... C07D 513/04; C07D 285/36; A61K 31/55
[52] U.S. Cl. .................................................. 540/545
[58] Field of Search ................................. 540/545

[56] References Cited

U.S. PATENT DOCUMENTS 5,294,720  3/1994  Jadhav et al. .................... 546/256

FOREIGN PATENT DOCUMENTS

| 501568 | 9/1992 | European Pat. Off. | 540/545 |
| WO9323361 | 11/1993 | WIPO | 424/238 |
| WO9307128 | 11/1993 | WIPO | 540/545 |
| WO9419329 | 9/1994 | WIPO | 540/545 |

*Primary Examiner*—Robert T. Bond
*Attorney, Agent, or Firm*—Blair Q. Ferguson

[57] ABSTRACT

The present invention discloses processes for the preparation of substituted cyclic sulfamides which are useful as intermediates for the synthesis of cyclic sulfamide human immunodeficiency virus (HIV) protease inhibitors. Such substituted cyclic sulfamide intermediates contain a cyclic acetal-protected diol.

25 Claims, No Drawings

METHOD FOR PREPARING CYCLIC SULFAMIDES AND THEIR USE FOR THE SYNTHESIS OF HIV PROTEASE INHIBITORS

CROSS-REFERENCE TO EARLIER FILED APPLICATIONS

This application is a continuation-in-part of U.S. patent application Ser. No. 08/197,630 filed Feb. 16, 1994, which is a continuation-in-part of U.S. patent application Ser. No. 08/047,330, now abandoned, filed Apr. 15, 1993, which is a continuation-in-part of U.S. patent application Ser. No. 08/023,439, filed Feb. 26, 1993, now abandoned. The disclosure of these earlier filed applications is hereby incorporated herein by reference.

FIELD OF THE INVENTION

The present invention relates generally to processes for the preparation of substituted cyclic sulfamides which are useful as intermediates for the synthesis of cyclic sulfamide human immunodeficiency virus (HIV) protease inhibitors. Such substituted cyclic sulfamide intermediates contain a cyclic acetal-protected diol.

BACKGROUND OF THE INVENTION

Moore, *Biochem. Biophys. Res. Commun.*, 159 420 (1989) discloses peptidyl inhibitors of HIV protease. Erickson, European Patent Application No. WO 89/10752 discloses derivatives of peptides which are inhibitors of HIV protease.

U.S. Pat. No. 4,652,552 discloses methyl ketone derivatives of tetrapeptides as inhibitors of viral proteases. U.S. Pat. No. 4,644,055 discloses halomethyl derivatives of peptides as inhibitors of viral proteases. European Patent Application No. WO 87/07836 discloses L-glutamic acid gamma-monohydroxamate as an antiviral agent.

Jadhav et al., *Bioorganic & Med. Chem. Lett* 2(4) 353–356 (1992), and Dreyer et al., *Biochemistry* 32 (3) 937–47 (1993), disclose symmetric linear HIV-1 protease inhibitors which contain an acetonide protecting group.

Jadhav et al., U.S. Pat. No. 5,294,720 discloses the preparation of linear unprotected or acetonide protected diaminodihydroxyalkanes and amino acid and peptide derivatives thereof as retroviral protease inhibitors.

Jadhav et al., *Bioorganic & Med. Chem. Lett* 2(4) 353–356 (1992), and Chenera et al., *Bioorg. Med. Chem. Lett.* 1(4) 219–22 (1991), disclose the synthesis of C2-symmetric and pseudosymmetric HIV-1 protease inhibitors from D-mannitol and D-arabitol.

European Patent Application No. EP 486948 discloses linear diaminohydroxy compounds useful as HIV-1 protease inhibitors.

European Patent Application No. EP 501568-A1 discloses cyclic sulfamide compounds useful as 5-HT1 receptor agonists.

Lam et al., PCT International Publication Number WO 93/07,128 discloses cyclic carbonyl compounds and derivatives thereof which are useful as human immunodeficiency virus (HIV) protease inhibitors for the treatment of HIV infection. The compounds disclosed in WO 93/07128 include cyclic HIV protease inhibitor compounds of the formula below where W may be —N($R^{22}$)C(=O)N($R^{23}$)— or —N($R^{22}$)S(=O)N($R^{23}$)—.

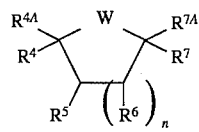

Copending commonly assigned U.S. patent applications Ser. No. 08/197,630 filed Feb. 16, 1994, Ser. No. 08/047,330, filed Apr. 15, 1993, and Ser. No. 08/023,439, filed Feb. 26, 1993, disclose cyclic HIV protease inhibitors, including cyclic sulfamide HIV protease inhibitors, of the formula below wherein W may be —N($R^{22}$)S(=O)$_2$N($R^{23}$)—.

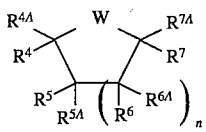

As disclosed in the above copending commonly assigned patent applications, such cyclic sulfamide compounds, which may be made using the processes of the present invention, are non-peptidic, low molecular weight, orally bioavailable compounds useful as inhibitors of HIV protease and for the treatment of HIV infection. The HIV protease inhibitory activity of the cyclic sulfamide can be increased by two to three orders of magnitude by alkylating one or both of the urea nitrogens.

Consequently, a need exists for more efficient and cost-effective methods for the preparation of the cyclic sulfamide HIV protease inhibitor compounds of the above copending commonly assigned patent applications in high yields from readily available starting materials. The present invention provides improved processes for the synthesis of such cyclic sulfamide HIV protease inhibitor compounds.

SUMMARY OF THE INVENTION

The present invention comprises processes for the preparation of substituted cyclic sulfamides of formula (III) (shown below) having a diol protected with a cyclic acetal (or ketal) group. Such cyclic acetal-protected cyclic sulfamides are useful as intermediates for the formation of cyclic sulfamide compounds of formula (IV) (shown below) which are useful as inhibitors of human immunodeficiency virus (HIV) protease. Thus, such cyclic acetal-protected cyclic sulfamide compounds may be deprotected to form diol-containing cyclic sulfamide HIV protease inhibitors, which are useful for the inhibition of HIV and treatment of HIV infection.

The present invention comprises a process for the preparation of compounds of formula (III)

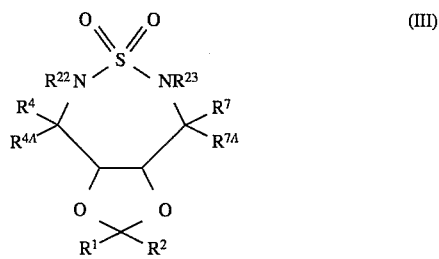

or a pharmaceutically acceptable salt or prodrug form thereof, wherein $R^{22}$, $R^{23}$, $R^4$, $R^{4A}$, $R^7$, $R^{7A}$, $R^1$, and $R^2$ are defined below, comprising the steps of: (1) contacting a compound of formula (I) or (IA) (IB):

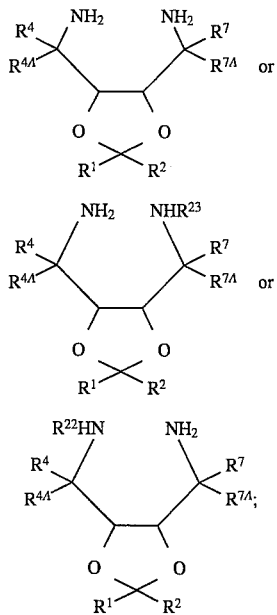

(I)

(IA)

(IB)

wherein $R^{22}$, $R^{23}$, $R^4$, $R^{4A}$, $R^7$, $R^{7A}$, $R^1$, and $R^2$ are defined below, in a solution with a hindered amine base and a —S(=O)$_2$— precursor to obtain a compound of the formula (II) or (IIA) or (IIB);

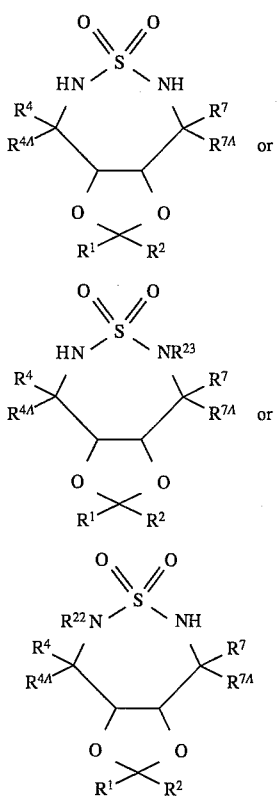

(II)

(IIA)

(IIB)

(2) contacting the compound of formula (II) or (IIA) or (IIB) of step (1) above, with a suitable base and an alkylating agent of formula $R^{22}$—Y or $R^{23}$—Y, where Y is a suitable leaving group, to obtain a compound of formula (III).

The present invention also comprises a process for the formation of a compound of formula (IV):

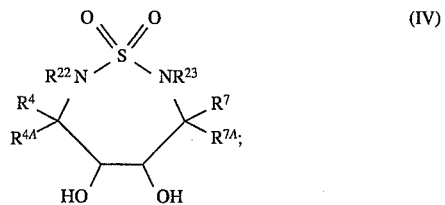

(IV)

comprising steps (1) and (2) above and the additional step (3) comprising:

(3) treatment of the compound of formula (III) of step (2) above under conditions effective to remove the cyclic acetal protecting group, to obtain a compound of formula (IV).

DETAILED DESCRIPTION OF THE INVENTION

The present invention provides processes for the preparation of substituted cyclic sulfamides of formula (III) having a diol protected with a cyclic acetal (or ketal) group. As used herein, the term cyclic acetal is intended to also refer to cyclic ketal groups. Such cyclic acetal-protected cyclic sulfamides are useful as intermediates for the formation of cyclic sulfamide compounds of formula (IV) which are useful as inhibitors of HIV protease. Thus, such cyclic acetal-protected cyclic sulfamide compounds may be deprotected to form diol-containing cyclic sulfamide HIV protease inhibitors, which are useful for the inhibition of HIV and treatment of HIV infection.

In the process of the present invention, a compound of formula (I) or (IA) or (IB) is cyclized to afford either a non-N-alkylated or mono-N-alkylated compound of formula (II) or (IIA) or (IIB), respectively. The compound of formula (II) or (IIA) or (IIB) may then be alkylated to afford a symmetrically or unsymmetrically N-alkylated compound of formula (III).

The present invention comprises a process for the preparation of compounds of formula (III)

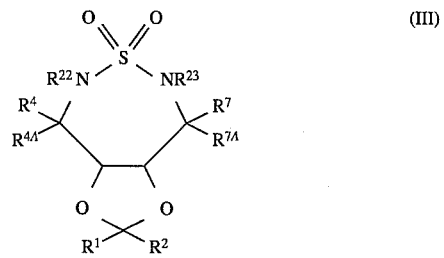

(III)

or a pharmaceutically acceptable salt or prodrug form thereof wherein:

$R^4$ and $R^7$ are independently selected from the following groups:

hydrogen;

$C_1$–$C_8$ alkyl substituted with 0–3 $R^{11}$;

$C_2$–$C_8$ alkenyl substituted with 0–3 $R^{11}$;

$C_2$–$C_8$ alkynyl substituted with 0–3 $R^{11}$;

a $C_3$–$C_{14}$ carbocyclic ring system substituted with 0–3 $R^{11}$ or $R^{12}$;

a 5- to 10-membered heterocyclic ring system containing 1 to 4 heteroatoms independently selected from oxygen, nitrogen or sulfur, said heterocyclic ring system being substituted with 0–2 $R^{12}$;

—$OR^{13}$; —$SR^{13}$; $CO_2R^{13}$;

$R^{4A}$ and $R^{7A}$ are independently selected from the following groups:

hydrogen;

$C_1$–$C_4$ alkyl substituted with $C_1$–$C_2$ alkoxy;

benzyl substituted with $C_1$–$C_2$ alkoxy;

—$OR^{13}$; —$SR^{13}$; $CO_2R^{13}$;

$R^4$ and $R^{4A}$ can alternatively join to form a 5–7 membered carbocyclic ring substituted with 0–2 $R^{12}$;

$R^7$ and $R^{7A}$ can alternatively join to form a 5–7 membered carbocyclic ring substituted with 0–2 $R^{12}$;

$R^1$ and $R^2$ are independently H, $C_1$–$C_4$ alkyl, $C_1$–$C_4$ alkoxy, $C_6$–$C_{10}$ aryl, $C_7$–$C_{14}$ arylalkyl, $C_3$–$C_7$ cycloalkyl, or, alternately, $R^1$ and $R^2$ can be taken together with the carbon to which they are attached to form a 3–7 membered saturated carbocyclic ring system;

$R^{11}$ is selected from one or more of the following:

H, keto, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$,=$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$ —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl (O-protected), methylenedioxy, ethylenedioxy, $C_1$–$C_4$ alkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;

1–3 amino acids linked together via amide bonds, and said amino acid being linked to $R^4$ or $R^7$ via the amine or carboxylate terminus;

—($C_1$–$C_3$ alkyl)aryl substituted with 0–2 $R^{12}$;

a $C_5$–$C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:

H, keto, cyano, —$CH_2NH_2$, —$NH_2$, —$CO_2H$, —$OC(=O)$ ($C_1$–$C_3$ alkyl), —OH, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl (O-protected), methylenedioxy, ethylenedioxy, $C_1$–$C_4$ alkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system;

$R^{12}$ when a substituent on carbon, is selected from one or more of the following:

phenyl, benzyl, phenethyl, phenoxy, benzyloxy, O-protected hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl $C_1$–$C_4$ hydroxyalkyl (O-protected), methylenedioxy, ethylenedioxy, $C_1$–$C_4$ alkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2^{R14}$, —$OCH_2CO_2H$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6-membered ring being optionally substituted on the aliphatic carbons with $C_1$–$C_4$ alkyl, $C_1$–C4 alkoxy, O-protected hydroxy, or —$NR^{13}R^{14}$; or, when $R^{12}$ is attached to a saturated carbon atom, it may be =O or =S;

$R^{12}$ when a substituent on nitrogen, is selected from one or more of the following:

phenyl, benzyl, phenethyl, O-protected hydroxy, $C_1$–$C_4$ hydroxyalkyl (O-protected), $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{13}$ is selected from:

phenyl substituted with 0–3 $R^{11A}$;

benzyl substituted with 0–3 $R^{11A}$;

$C_1$–$C_6$ alkyl substituted with 0–3 $R^{11A}$;

$C_2$–$C_4$ alkenyl substituted with 0–3 $R^{11A}$;

$C_1$–$C_6$ alkylcarbonyl substituted with 0–3 $R^{11A}$;

$C_1$–$C_6$ alkoxycarbonyl substituted with 0–3 $R^{11A}$;

$C_1$–$C_6$ alkylaminocarbonyl substituted with 0–3 $R^{11A}$;

$C_3$–$C_6$ alkoxyalkyl substituted with 0–3 $R^{11A}$;

an amine protecting group when $R^{13}$ is bonded to N;

a hydroxy protecting group when $R^{13}$ is bonded to O;

$R^{14}$ is selected from:

$CF_3$;

$C_1$–$C_6$ alkyl substituted with 0–3 groups selected from —O—SEM, $C_1$–$C_4$ alkoxy, —$NHCO_2Bu^t$, —$N(C_1$–$C_4$ alkyl)-$CO_2Bu^t$;

$C_1$–$C_6$ alkoxy;

—NH—$CO_2Bu^t$;

$C_2$–$C_6$ alkenyl;

benzyl;

an amine protecting group when $R^{14}$ is bonded to N;

a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

$R^{22}$ and $R^{23}$ are independently selected from the following:

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–2 $R^{32}$;

—$OR^{22a}$, —$N(R^{22a})(R^{22b})$;

$R^{22a}$ and $R^{22b}$ are independently selected from the following:

hydrogen;

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–2 $R^{32}$;

$R^{31}$ is selected from one or more of the following:

ketal, acetal, cyano, —$CH_2NR^{13}R^{14}$, —$NR^{13}R^{14}$, —$CO_2Bu^t$, —$C(=O)R^{11}$, —$C(OR^{22a})_2$—$R^{11}$, —$OR^{13}$, $C_2$–$C_6$ alkoxyalkyl, —$S(O)_mR^{13}$, —$N(SEM)C(=NSEM)N(SEM)R^{13}$, —$C(=NSEM)N(SEM)R^{13}$, —$C(=O)NR^{13}R^{14}$, —$NR^{14}C(=O)R^{13}$, $=NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, SEM protected oxime, SEM protected sulfonamide, formyl, $C_3$–$C_6$ cycloalkoxy, $C_1$–$C_4$ alkyl substituted with —$NR^{13}R^{14}$, $C_1$–$C_4$ SEM protected hydroxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})=N(OR^{14})$; or 1–3 amino acids, linked together via amide bonds, and said amino acid being linked to $R^{22}$ or $R^{23}$ via the amine or carboxylate terminus;

a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3$–$C_{10}$ cycloalkyl, $C_3$–$C_6$ cycloalkylmethyl, $C_7$–$C_{10}$ arylalkyl, BOC protected hydrazide, benzyl protected oxime, $C_2$–$C_6$ alkoxyalkyl, methylenedioxy, ethylenedioxy, $C_1$–$C_4$ alkylcarbonyloxy, —$NHSO_2R^{14}$, benzyloxy, 2-(1-morpholino)ethoxy, —$CO_2Bu^t$, —$CONR^{13}NR^{13}R^{14}$, cyano, boronic acid, sulfonamide, —$CHO$, $C_3$–$C_6$ cycloalkoxy, —$NR^{13}R^{14}$, —$C(R^{14})=N(OR^{14})$ $NO_2$, —$OR^{13}$ —$NR^{40}R^{41}$, —$SO_mR^{13}$, —$SO_m NR^{13}R^{14}$, —$C(=O)NR^{13}R^{14}$, —$OC(=O)NR^{13}R^{14}$, —$C(=O)R^{11}$, phenyl, —$C(=O)NR^{13}$—$(C_1$–$C_4$ alkyl) —$NR^{13}R^{14}$, —$C(=O)NR^{40}R^{41}$, or

—$C(=O)NR^{13}C(R^{11})_2NR^{13}R^{14}$;

—$C(=O)NR^{13}C(R^{11})_2NR^{13}NR^{14}$;

—$C(=O)NR^{13}C(R^{11})_2NR^{13}CO_2R^{13}$;

—$C(=O)NR^{13}$—$(C_1$–$C_4$ alkyl)—$NR^{13}CO_2R^{13}$;

—$C(=O)N(R^{13})$—$(C_1$–$C_4$ alkyl)—$R^{11}$; or

—$C(=O)C(R^{11})_2NR^{13}R^{14}$;

—$C(=O)C(R^{11})_2NR^{13}NR^{14}$;

—$C(=O)C(R^{11})_2NR^{13}CO_2R^{13}$; —$C(=O)$—$(C_1$–$C_4$ alkyl)—$NR^{13}R^{14}$; —$C(=O)$—$(C_1$–$C_4$ alkyl)—$NR^{13}CO_2R^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH;

$C_1$–$C_4$ alkyl substituted with 0–4 groups selected from: $R^{11}$, $=NR^{14}$, $=NNR^{13}C(=O)NR^{13}R^{14}$ or —$NR^{13}R^{14}$;

$C_2$–$C_4$ alkenyl substituted with 0–4 $R^{11}$;

$C_2$–$C_4$ alkynyl substituted with 0–4 $R^{11}$;

a 5- or 6-membered heterocyclic ring containing from 1 to 4 heteroatoms independently selected from oxygen, nitrogen or sulfur;

or $R^{32}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, benzyloxy, or —$NR^{13}R^{14}$; or, when $R^{32}$ is attached to a saturated carbon atom, it may be $=O$, $=NO$benzyl or $=S$;

$R^{32}$, when a substituent on nitrogen, is selected from one or more of the following:

phenyl, benzyl, phenethyl, O-protected hydroxy, $C_1$–$C_4$ hydroxyalkyl (O-protected), $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{40}$ is selected from: $C_1$–$C_3$ alkyl;

$R^{41}$ is selected from:

—$C(=O)NR^{13}R^{14}$;

—$C(=O)NR^{13}NR^{14}$;

—$C(=O)C(R^{11})_2NR^{13}R^{14}$;

—$C(=O)C(R^{11})_2NR^{13}NR_{14}$;

—$C(=O)C(R^{11})_2NR^{13}CO_2R^{13}$;

—$C(=O)H$;

—$C(=O)R^{11}$;

—$C(=O)$—$(C_1$–$C_4$ alkyl)—$NR^{13}R^{14}$;

—$C(=O)$—$(C_1$–$C_4$ alkyl)—$NR^{13}CO_2R^{13}$;

1–3 amino acids linked together via amide bonds, and linked to the N atom via the carboxylate terminus;

with the proviso that: $R^4$, $R^{4A}$, $R^7$ and $R^{7A}$ are not all hydrogen;

said process comprising the steps of:

(1) contacting a compound of formula (I) or (IA) (IB):

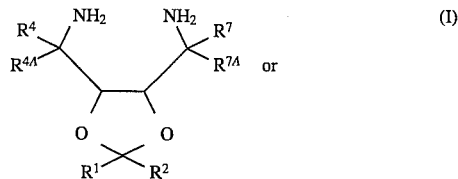

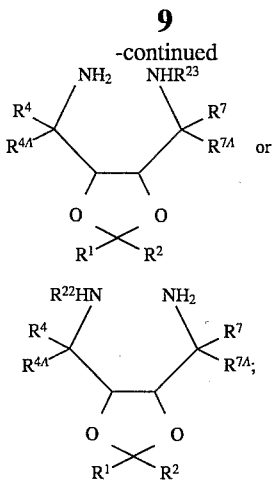

(IA)

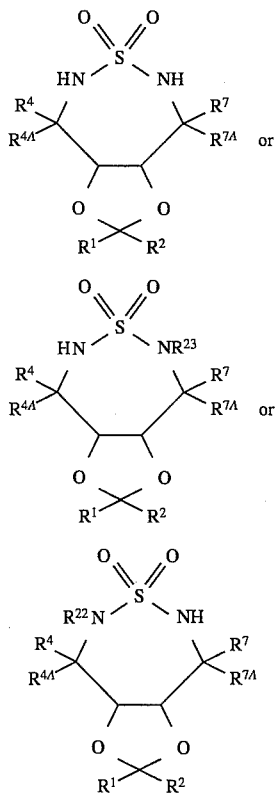

(IB)

wherein $R^{22}$, $R^{23}$, $R^4$, $R^{4A}$, $R^7$, $R^{7A}$, $R^1$ and $R^2$ are defined above, in a solution with a hindered amine base and a —S(=O)$_2$— precursor to obtain a compound of the formula (II) or (IIA) or (IIB);

(II)

(IIA)

(IIB)

(2) contacting the compound of formula (II) or (IIA) or (IIB) of step (1) above, with a suitable base and an alkylating agent of formula $R^{22}$—Y or $R^{23}$—Y, where Y is a suitable leaving group, to obtain a compound of formula (III).

In the above process of the present invention, all functional groups in $R^{22}$, $R^{23}$, $R^4$, $R^{4A}$, $R^7$, and $R^{7A}$, that are reactive with the —S(=O)$_2$— precursor under the conditions of step (1) are protected with suitable protecting groups prior to carrying out step (1) thereby to prevent reaction with the —S(=O)$_2$— precursor. Such protecting groups may be removed after step (1) is completed or may removed after step (2) is completed. The use of such protecting groups is well understood by one of skill in the art of synthetic organic chemistry.

Similarly, all functional groups in $R^{22}$, $R^{23}$, $R^4$, $R^{4A}$, $R^7$, and $R^{7A}$, that are reactive with the alkylating agent under the conditions of step (2) are protected with suitable protecting groups prior to carrying out step (2) thereby to prevent reaction with the alkylating agent. Such protecting groups may be the same or different than the protecting group used in step (1). Such protecting groups may be removed after step (2) is completed to yield a compound of formula (III) or (IV) wherein the protected groups are deprotected, or, alternatively, may be removed in step (3) to yield a compound of formula (IV), wherein the protected groups are deprotected.

Preferred in the present invention is the above process wherein:

$R^1$ and $R^2$ are independently H, $C_1$–$C_4$ alkyl, or, alternately, $R^1$ and $R^2$ can be taken together with the carbon to which they are attached to form a 5–6 membered saturated carbocyclic ring system;

$R^4$ and $R^7$ are independently selected from the following groups:

hydrogen;

$C_1$–$C_8$ alkyl substituted with 0–3 $R^{11}$;

$C_2$–$C_8$ alkenyl substituted with 0–3 $R^{11}$;

$C_2$–$C_8$ alkynyl substituted with 0–3 $R^{11}$;

$R^{4A}$ and $R^{7A}$ are hydrogen;

$R^{11}$ is selected from one or more of the following:

H, keto, cyano, —CH$_2$NR$^{13}$R$^{14}$, —NR$^{13}$R$^{14}$, —OR$^{13}$, —S(O)$_m$R$^{13}$, $C_1$–$C_4$ alkyl, $C_2$–$C_4$ alkenyl, $C_3$–$C_{10}$ cycloalkyl substituted with 0–2 $R^{12}$, a $C_5$–$C_{14}$ carbocyclic residue substituted with 0–3 $R^{12}$, aryl($C_1$–$C_3$ alkyl)—, substituted with 0–2 $R^{12}$, aryl substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$ when a substituent on carbon, is selected from one or more of the following:

phenyl, benzyl, phenethyl, phenoxy, benzyloxy, O-protected hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —OR$^{13}$, $C_1$–$C_4$ alkyl substituted with —NR$^{13}$R$^{14}$, —NR$^{13}$R$^{14}$, $C_2$–$C_6$ alkoxyalkylene optionally substituted with —Si (CH$_3$)$_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$R$^{13}$, —SO$_2$NR$^{13}$R$^{14}$, —NHSO$_2$R$^{14}$, 2-(1-morpholino)ethoxy, —C(R$^{14}$)=N(OR$^{14}$); or a 5- or 6-membered heterocyclic ring containing from to 4 heteroatoms independently selected from oxygen, nitrogen or sulfur;

or $R^{12}$ may be a 3- or 4- carbon chain attached to adjacent carbons on the ring to form a fused 5- or 6membered ring, said 5- or 6- membered ring being optionally substituted on the aliphatic carbons with $C_1$–$C_4$ alkyl, $C_1$–$C_4$ alkoxy, O-protected hydroxy, or —NR$^{13}$R$^{14}$; or, when $R^{12}$ is attached to a saturated carbon atom, it may be =O or =S; or when $R^{12}$ is attached to sulfur it may be =O;

$R^{12}$ when a substituent on nitrogen, is selected from one or more of the following:

phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$NR$^{13}$R$^{14}$, —NR$^{13}$R$^{14}$, $C_2$–$C_6$ alkoxyalkyl, $C_1$–$C_4$ alkylcarbonyl, —C(R$^{14}$)=N(OR$^{14}$);

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a hydroxy protecting group when $R^{14}$ is bonded to O;

m is 0, 1 or 2;

$R^{22}$ and $R^{23}$ are independently selected from the group consisting of: hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloromethylthienyl, benzyloxybenzyl, phenylbenzyl, adamantylethyl, cyclopropylmethoxybenzyl, methoxybenzyl, methylbenzyl, ethoxybenzyl, benzyloxybenzyl, hydroxymethylbenzyl (with suitable protecting group), aminobenzyl (with suitable protecting group), formylbenzyl, cyanobenzyl, cinnamyl, allyloxybenzyl, fluorobenzyl, difluorobenzyl, chlorobenzyl, iodobenzyl, bromobenzyl, cyclobutylmethyl, formaldoximebenzyl, cyclopentylmethyl, nitrobenzyl, carbo-t-butoxybenzyl, tetrazolylbenzyl, dimethylallyl, 2,5-dimethyl-N-pyrrolylmethylbenzyl, (O-benzylformaldoxime) benzyl, (O-methyl-formaldoxime) benzyl, (benzyl—$OCH_2CH_2N=CH$)—benzyl, $(CH_3)_3OCON(CH_3)$benzyl, $(CH_3)_3OCON$benzyl $(CH_3)_3OCON(CH2CH_3)$benzyl, $(CH_3)_3OCON(CH_2CH_3)$methylbenzyl, p-(1,1-dimethoxy)ethylbenzyl, N-benzyloxyaminobenzyl, N-benzyloxyethylbenzyl, $(CH_3C(=NO$-benzyl$))$-benzyl, $(CH_3ONHC(=O))$-benzyl, (benzyl-$ONHC(=O)$)-benzyl, $(CH_3NHC(=O))$-benzyl, N,N-dimethylaminocarbonylbenzyl, (benzyl-$OCH_2CH$(O-benzyl) $CH_2O$) -benzyl, benzyloxyethoxybenzyl (oxazolidinyl) -benzyl, (benzyloxyl) hexyl, hexenyl, (benzyloxy) octyl, (benzyloxyl)pentyl, (carbo-t-butoxy) pentyl, N, N-dimethylaminomethylbenzyl, (N-phenylmethoxycarbonyl)alanylaminobenzyl, phenylalanylaminobenzyl, (N-phenylmethoxycarbonyl) phenylalanylaminobenzyl, $(CH_3CH_2NHC(=O))$ -benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (benzyloxypropynyl)benzyl, (imidazolyl-$C(=O)$) benzyl, (pyrazolyl-$C(=O)$) -benzyl, (pyridylmethylaminocarbonyl)benzyl, (oxadiazolidinonyl)benzyl, trifluoroacetylbenzyl, pyrazolylbenzyl (sem protected), 1,2-dibenzyloxyethylbenzyl, methanesulfonylpentyl, methoxypentyl, N-formyl-N-methylaminobenzyl, acetylaminobenzyl, propionylbenzyl, butyrylbenzyl, $(CH_3CH_2C(=NO$-benzyl$))$-benzyl, $(CF_3C(=NO$-benzyl$))$benzyl, (N-methylglycyl)aminobenzyl, ((4-morpholino) ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-$NHC(=O)O$)benzyl, $(CH_3NHC(=O)O)$ benzyl, ((N-phenylmethoxycarbonyl)glycylamino)benzyl, (imidazolylmethyl)benzyl, $((CH_3)_3C-C(=O))$benzyl, (N-methyl-N-ethylaminoethyl)aminocarbonylbenzyl, (pyrrolidinylethyl)aminocarbonylbenzyl, (piperidinylethyl)aminocarbonylbenzyl, benzimidazolylmethyl, benzotriazolylmethyl, indazolylmethyl, benzoxazolinylmethyl, benzisoxazolylmethyl, thienylmethyl, or furylmethyl.

More preferred in the present invention is the above method wherein:

$R^1$ and $R^2$ are independently methy, ethyl, or, alternately, $R^1$ and $R^2$ can be taken together with the carbon to which they are attached to form cyclopentyl;

$R^4$ and $R^7$ are independently selected from: benzyl, fluorobenzyl, pyrrolylmethyl, methoxybenzyl, isobutyl, nitrobenzyl, N-protected aminobenzyl, thienylmethyl, O-protected hydroxybenzyl, pyridylmethyl, or naphthylmethyl;

$R^{4A}$ and $R^{7A}$ are hydrogen;

$R^{22}$ and $R^{23}$ are independently selected from: 4-hydroxy methylbenzyl (with base stable hydroxy protecting group), 3-hydroxybenzyl (with base stable hydroxy protecting group), cyclopropylmethyl, butyl, 2-naphthylmethyl, 4-hydroxybenzyl (with base stable hydroxy protecting group), 3-aminobenzyl (with base stable hydroxy protecting group), 3-hydroxymethylbenzyl (with base stable hydroxy protecting group), 3-$((CH_3)_2NCH_2C(=O)NH)$-benzyl, 3-$(C=NO$-benzyl$)$ benzyl, 3-$(CH_3C(=NO$-benzyl$))$-benzyl, m-(3-pyrazolyl)benzyl, P-(3-pyrazolyl)benzyl, benzindazolymethyl, 3-aminobenzindazolymethyl (with base stable N protecting group).

Further preferred is the above process wherein:

$R^1$ and $R^2$ are methyl;

$R^4$ and $R^7$ are independently selected from: benzyl, fluorobenzyl, pyrrolylmethyl, methoxybenzyl, isobutyl, nitrobenzyl, aminobenzyl (with amino protecting group), thienylmethyl, hydroxybenzyl (with base stable hydroxy protecting group), pyridylmethyl, naphthylmethyl, 4-N,N-dimethylaminobenzyl, 3-N,N-dimethylaminobenzyl, 4-thiazolylmethyl;

$R^{4A}$ and $R^{7A}$ are hydrogen;

$R^{22}$ is 5-hydroxypentyl (with base stable hydroxy protecting group) cyclopropylmethyl, butyl, betanaphthylmethyl;

$R^{23}$ is 2-naphthylmethyl, 4-hydroxymethylbenzyl (with base stable hydroxy protecting group), 3-hydroxymethylbenzyl (with base stable hydroxy protecting group), m-(3-pyrazolyl)benzyl, P-(3-pyrazolyl)benzyl, benzindazolymethyl, 3-aminobenzindazolymethyl (with base stable N protecting group).

The present invention also comprises a process for the preparation of compounds of formula (III) or (IV):

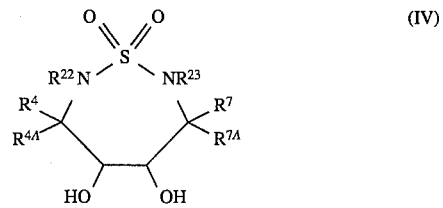

(IV)

or a pharmaceutically acceptable salt or prodrug form thereof, wherein $R^{22}$, $R^{23}$, $R^4$, $R^{4A}$, $R^7$, $R^{7A}$, $R^1$, and $R^2$ are defined as above, comprising one or more of the steps of:

(1) contacting a compound of formula (IC):

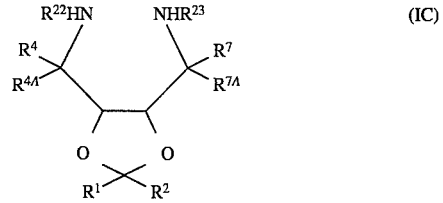

(IC)

wherein $R^{22}$, $R^{23}$, $R^4$, $R^{4A}$, $R^7$, $R^{7A}$, $R^1$, and $R^2$ are defined above, in a solution with a hindered amine base and a —S(=O)$_2$— precursor to obtain a compound of the formula (III):

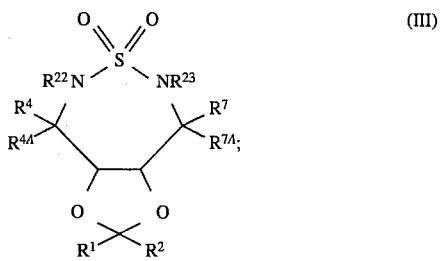

(2) treatment of the compound of formula (III) of step (1) above under conditions effective to remove the cyclic acetal protecting group, to obtain a compound of formula (IV), as defined above.

The processes of the present invention are useful for the preparation of compounds useful as intermediates for the synthesis of cyclic HIV protease inhibitors, including cyclic urea HIV protease inhibitors. Such cyclic HIV protease inhibitors are disclosed in copending commonly assigned U.S. patent application Ser. No. 08/197,630, Lam et al., filed Feb. 16, 1994 and Lam et al., PCT International Publication Number WO 93/07,128, the disclosures of which are incorporated herein by reference. Such cyclic HIV protease inhibitors are useful for the inhibition of HIV and the treatment of HIV infection. Such cyclic HIV protease inhibitors are also useful for the inhibition of HIV in an ex vivo sample containing HIV or expected to be exposed to HIV. Thus, such cyclic HIV protease inhibitors may be used to inhibit HIV present in a body fluid sample (for example, a serum or semen sample) which contains or is suspected to contain or be exposed to HIV. Such cyclic HIV protease inhibitors are also useful as standard or reference compounds for use in tests or assays for determining the ability of an agent to inhibit vital replication and/or HIV protease, for example in a pharmaceutical research program. Thus, such cyclic HIV protease inhibitors may be used as a control or reference compound in such assays and as a quality control standard. Such cyclic HIV protease inhibitors may be provided in a commercial kit or container for use as such standard or reference compound. Since such cyclic HIV protease inhibitors exhibit specificity for HIV protease, they may also be useful as diagnostic reagents in diagnostic assays for the detection of HIV protease. Thus, inhibition of the protease activity in an assay by such a cyclic HIV protease inhibitor would be indicative of the presence of HIV protease and HIV virus.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. Depending on the particular reaction step, suitable solvents for a particular reaction step may be selected and may include aprotic solvents, including but not limited to polar aprotic organic solvents. Depending on the particular reaction step, suitable solvents for a particular reaction step may be selected and may include, but are not limited to, toluene, pyridine, dimethylsulfoxide (DMSO), N,N-dimethylformamide (DMF), N,N-dimethylacetamide (DMAC), diethyl ether, benzene, or tetrahydrofuran. Suitable solvents may include chlorinated organic solvents which include, but are not limited to, chloroform, methylene chloride, tetrachloroethane, butyl chloride and dichloroethane. Suitable non-chlorinated organic solvents may include, but are not limited to tetrahydrofuran (THF), diethyl ether and toluene.

Suitable protic solvents may include, by way of example and without limitation, water, methanol, and ethanol.

Suitable aprotic solvents may include, by way of example and without limitation, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), tetrahydrofuran (THF), methylene chloride, dimethoxyethane, ether, or hexanes.

As used herein, the term "cyclic acetal protecting group" includes any protecting group known in the art of organic synthesis for the protection of 1,2-diol group through formation of a cyclic acetal or cyclic ketal group. Such protecting groups include, but are not limited to, those listed in Greene and Wuts, "Protective Groups in Organic Synthesis", John Wiley & Sons, New York (1991), the disclosure of which is hereby incorporated by reference. Exemplary are methylene acetal, ethylidene acetal, 2,2,2-trichloroethylidene acetal, acetonide, cycloheptylidene ketal, cyclopentylidene ketal, cyclohexylidene ketal, benzylidene acetal, phenanthrylidene, and methoxymethylene acetal.

By "—S(=O)$_2$— precursor" it is meant a reagent or combination of reagents and conditions that can effect the formation of a cyclic sulfamide from the diamine of formula (I), (IA), or (IB). Examples of suitable —S(=O)$_2$— precursors include but are not limited to: sulfamide; SO$_2$Cl$_2$; imidazole-S (=O)$_2$-imidazole; or SOCl$_2$ followed by oxidation of the cyclic —S(=O)— to —S (=O)$_2$—.

As used herein, a "hindered amine base" is intended to include any of a number of nitrogen containing bases wherein the nitrogen in surrounded by sterically demanding groups such that the nitrogen accessibility is reduced. Examples of hindered amine bases useful for the present invention include, by way of example and without limitation, aromatic and aliphatic amines, alkyl substituted pyridines, 1,8-diazabicyclo[2.2.2]octane (DABCO), pyridine, 4-pyrrolidinopyridine, 4-piperidinopyridine, N,N-dimethylaminopyridine (DMAP), trialkyl amines, triethylamine, N,N-diisopropylethylamine, 1,5-diazabicyclo [4.3.0 ]non-5-ene (DBN), 1,8-diazabicyclo[5.4.0]undec-7-ene (DBU), or tetramethylethylenediamine (TMEDA).

As used herein, the term "alkyating agent" refers to compounds of the formula $R^{22}Y$ and $R^{23}Y$, wherein Y is any common leaving group known to those skilled in the art. Y may be, by way of example and without limitation, a halogen, triflate, tosylate, nosylate or mesylate. Y is preferably a bromide, chloride or iodide. Suitable alkylating agents are disclosed in copending commonly assigned U.S. patent application Ser. No. 08/040,146, Jadhav et al., filed May 30, 1993, the disclosure of which is hereby incorporated by reference.

As used herein, the term "amine protecting group" (or "N-protected") refers to any group known in the art of organic synthesis for the protection of amine groups. Such amine protecting groups include those listed in Greene and Wuts, "Protective Groups in Organic Synthesis" John Wiley & Sons, New York (1991) and "The Peptides: Analysis, Synthesis, Biology," Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2)

aromatic carbamate types such as benzyloxycarbonyl (Cbz) and substituted benzyloxycarbonyls, 1- (p-biphenyl) -1-methylethoxycarbonyl, and 9-fluorenylmethyloxycarbonyl (Fmoc); 3) aliphatic carbamate types such as tertbutyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10 -dioxo-10,10,10, 10-tetrahydrothio-xanthyl)]methyl carbamate; 2-trimethylsilylethyl carbamate; 2-phenylethyl carbamate; 1,1-dimethyl-2,2-dibromoethyl carbamate; 1-methyl-l-(4-biphenylyl)ethyl carbamate; benzyl carbamate; p-nitrobenzyl carbamate; 2-(p-toluenesulfonyl)ethyl carbamate; m-chloro-p-acyloxybenzyl carbamate; 5-benzyisoxazolylmethyl carbamate; p-(dihydroxyboryl)benzyl carbamate; m-nitrophenyl carbamate; o-nitrobenzyl carbamate; 3,5-dimethoxybenzyl carbamate; 3,4-dimethoxy-6-nitrobenzyl carbamate; N'-p-toluenesulfonylaminocarbonyl; t-amyl carbamate; p-decyloxybenzyl carbamate; diisopropylmethyl carbamate; 2,2-dimethoxycarbonylvinyl carbamate; di(2-pyridyl)methyl carbamate; 2-furanylmethyl carbamate; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, the term "hydroxy protecting group" (or "O-protected") refers to any group known in the art of organic synthesis for the protection of hydroxyl groups. Such protecting groups include those listed in Greene and Wuts, "Protective Groups in Organic Synthesis" John Wiley & Sons, New York (1991), the disclosure of which is hereby incorporated by reference. The hydroxy protecting groups are base-stable and can include, but are not limited to acyl types, aromatic carbamate types and alkyl types. Exemplary are methyl, methoxymethyl (MOM), methylthiomethyl, benzyloxymethyl, t-butoxymethyl, 2-methoxyethoxymethyl, 2,2,2-trichloroethoxymethyl, 2-(trimethylsilyl)ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Suitable hydroxy protecting groups may include the following protecting groups as ethers: tetrahydropyranyl, triphenylmethyl, benzyl, tetrahydrofuranyl, allyl, methoxymethyl (MOM), benzyloxymethyl, p-methoxybenzyloxymethyl, 2-trimethylsilylethoxymethyl (SEM), t-butoxymethyl, methylthiomethyl, 2-methoxyethoxymethyl, trichloroethoxymethyl, t-butyl, p-methoxybenzyl, t-butyldimethylsilyl, o-nitrobenzyl, p-methoxyphenyldiphenylmethyl, p-nitrobenzyl, triisopropylsilyl, t-butyldiphenylsilyl.

Conditions to remove tetrahydropyranyl, triphenylmethyl, tetrahydrofuranyl, methoxymethyl, benzyloxymethyl, p-methoxybenzyloxymethyl, 2-trimethylsilylethoxymethyl, t-butoxymethyl, methylthiomethyl, 2-methoxyethoxymethyl, trichloroethoxymethyl, t-butyl, p-methoxyphenyldiphenylmethyl, may include: (a) 1–4M HCl in anhydrous or aqueous methanol, ethanol, isopropanol, tetrahydrofuran, dioxane, or diethyl ether; (b) 1–4M H2SO4 in anhydrous or aqueous methanol, ethanol, isopropanol, tetrahydrofuran, dioxane, or diethyl ether; (c) polystyrene sulfonic acid resin in anhydrous or aqueous methanol, ethanol, isopropanol, tetrahydrofuran, dioxane, or diethyl ether; (d) 10–100% trifluoroacetic acid in dichloromethane; or (e) p-toluenesulfonic acid or camphorsulfonic acid in anhydrous or aqueous methanol, ethanol, isopropanol.

Conditions to remove benzyl, benzyloxymethyl, p-methoxybenzyloxymethyl, p-methoxybenzyl, o-nitrobenzyl, p-nitrobenzyl are: hydrogenolysis in the presence of 1–17% palladium on carbon, or palladium black. Conditions to remove o-nitrobenzyl group include irradiation of the compound at 320 nm wavelength for 5– 60 minutes.

Conditions to remove 2-trimethylsilylethoxymethyl, t-butyldimethylsilyl, triisopropylsilyl, t-butyldiphenylsilyl may include: treatment of the compound with tetrabutylammonium fluoride; or hydrogen flouride pyridine complex in THF, DMF or dimethylpropyleneurea.

Conditions to remove allyl may include: isomerization of the allyl ether with [Ir(COD) (Ph$_2$MeP)$_2$]PF$_6$ or (Ph$_3$P)$_3$RhCl in tetrahydrofuran, diethyl ether or dioxane followed by hydrolysis with aqueous HgCl$_2$.

All of the above mentioned deprotection reactions may be carried out at temperetaures ranging from 0 degree C. to a solvent reflux.

The following abbreviations are also used herein and are defined as follows. The abbreviation "DIBAl" means diisobutylaluminum hydride. The abbreviation "RaNi" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "BOC" means t-butyl carbamate. The abbreviation "CBZ" means benzyl carbamate.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example $R^1$ through $R^{41}$, $R^{44}$ and $R^{74}$, m, n etc.) occurs more than one time in any constituent or in formula (I) or (II), or any other formula herein, its definition on each occurrence is independent of its definition at every other occurrence. Thus, for example, if a group is shown to be substituted with 0–3 $R^{11}$, then said group may optionally be substituted with up to three $R^{11}$ and $R^{11}$ at each occurrence is selected independently from the defined list of possible $R^{11}$. Also, combinations of substituents and/or variables are permissible only if such combinations result in stable compounds. Similarly, by way of example, for the group —C($R^{11}$)$_2$—, each of the two $R^{11}$ substituents on C is independently selected from the defined list of possible $R^{11}$.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —C$_v$F$_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

The terms "-(alkyl)-", "-(alkyenyl)-", "-(phenyl)-", and the like, refer to alkyl, alkenyl, and phenyl groups, respectively, which are connected by two bonds to the rest of the structure of Formula (II). Such groups may alternatively and equivalently be denoted as "alkylene", "alkenylene", "phenylene", and the like, respectively.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl., oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of a given formula via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids,such as those disclosed in, for example, Roberts and Vellaccio (1983) The Peptides, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The process of the present invention is described further below.

Step 1

This step comprises the cyclization of linear diaminediols of the formula (I), (IA), or (IB) by reaction with a $-S(=O)_2-$ precursor as described below. The compound of formula (I), (IA), or (IB) in solution is preferably reacted with at least about one molar equivalent of a $-S(=O)_2-$ precursor in the presence of a hindered amine base to form a cyclic sulfamide of the formula (II), (IIA), or (IIB), respectively. By way of general guidance, the reaction may be carried out at a temperature in the range of about 0° to 150° C. or the solvent reflux temperature, whichever is less. The reaction temperature is preferably in the range of about 10° C. to the solvent reflux temperature. The reaction pressure may be in the range from about 1–20 arm.

The reaction solvent may be polar, anhydrous, and non-reactive with the reactants and products. The reaction solvent may be, by way of example and without limitation, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), or tetrahydrofuran (THF).

The $-S(=O)_2-$ precursor may preferably be, for example but not limited to, sulfamide, $SO_2Cl_2$, imidazole-$S(=O)_2$-imidazole, or $SOCl_2$ followed by oxidation of the cyclic $-S(=O)-$ to $-S(=O)_2-$.

The $-S(=O)_2-$ precursor may be present in the range of about 0.5–3 molar equivalents, preferably about 0.9–1.1 molar equivalents, per equivalent of diaminediol (compound of formula (I), (IA), or (IB)). The diaminediol is taken to have 2 equivalent of amine per mole of diaminediol.

The hindered amine base may be, by way of example and without limitation, aromatic and aliphatic amines, alkyl substituted pyridines, 1,8-diazabicyclo[2.2.2]octane (DABCO), pyridine, 4-pyrrolidinopyridine, 4-piperidinopyridine, N,N-dimethylaminopyridine (DMAP), trialkyl amines, triethylamine, N, N-diisopropylethylamine, 1,5-diazabicyclo[4.3.0]non-5-ene (DBN), 1,8-diazabicyclo[5.4.0] undec-7-ene (DBU), or tetramethylethylenediamine (TMEDA). The hindered amine base may be present in the range of 0.1–10 equivalent per equivalent of diaminediol (formula (I), (IA), or (IB)). The hindered amine base may also be used as solvent. The reaction time may vary, for example, from about 10 min to 3 days.

A preferred reaction time for step (1) is about 1– 18 hr.

A preferred reaction solvents are DMF, DMAC, pyridine, and DMPU.

A preferred reaction pressure is about 1 atm.

A preferred reaction temperature is solvent reflux or about 150° C., whichever is less.

A preferred $-S(=O)_2-$ precursor is sulfamide.

The hindered amine base is preferably present in the range of about 0.01–20 equivalent/diaminediol equivalent or about 0.1–1.0 equivalent/diaminediol equivalent. A greater molar equivalent amount of the hindered amine base may be present when the solvent is also the hindered amine base, for example, when pyridine is used as the solvent and the hindered amine base.

The hindered amine base is preferably pyridine, 1,8-diazabicyclo[5.4.0]undec-7-ene (DBU), 1,8-diazabicyclo [2.2.2]octane (DABCO), 1,5-diazabicyclo[4.3.0]non-5-ene (DBN), or diisopropylethylamine.

Compounds of formula (I) may be prepared as described in Jadhav et al., U.S. Pat. No. 5,294,720; copending, commonly assigned patent application Ser. No. 08/197,630; and Lam et al., PCT International Publication Number WO 93/07,128; the disclosure of each of which is incorporated herein be reference.

Compounds of the formula (IA) or (IB) can be synthesized by alkylation of the compound of the formula (I) using methods known to skilled in the art. For example, compound of the formula (IA) or (IB) can be synthesized by contacting it with about 0.5 to 1 equivalent amount of $R^{22}$—Y or $R^{23}$—Y (wherein Y is suitable leaving group) in the presence of a suitable base (such as but not limited to: potassium or sodium carbonate; potassium or sodium hydride; potassium or sodium hydroxide; or potassium-t-butoxide), in an aprotic solvent (such as but not limited to: acetonitrile, dioxane, tetrahydrofuran, dimethylformamide).

Step (2)

Step (2) of the present invention comprises the alkylation of a partially (i.e., mono) N-alkylated or non-N-alkylated cyclic sulfamide, optionally in solution, at a suitable temperature under an appropriate pressure with an alkylating agent of the formula $R^{22}$—Y and/or $R^{23}$—Y, in the presence of a base catalyst, for a period of time to form a N-alkylated cyclic sulfamide of the formula (III). By way of general guidance the following conditions may preferably be used for the reaction of step (2). The reaction time may preferably be in the range of about 1 min to 7 days or 1 hr to 3 days, preferably about 12–18 hr. The reaction pressure may preferably be in the range of about 1–20 atm. The reaction temperature may preferably be in the range of about 0°–40° C.

If run in solution, the reaction solvent may be a polar aprotic solvent such as, by way of example and without limitation, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), tetrahydrofuran (THF). The reaction may optionally be run neat without added solvent.

Y in the alkylating agent is a suitable leaving group. The alkylating agent may be present in the range of about 0.5–20 equivalent/amine equivalent to be alkylated or about 2–10 equivalent/amine equivalent to be alkylated. The base catalyst may be present in the range of about 0.5–15 equivalent/equivalent of amine to be alkylated or about 2.5–5.0 equivalent/equivalent of amine to be alkylated. The base catalyst may be, for example, an alkali metal hydride, alkali metal hydroxide, alkali metal carbonate, or an alkali metal alkoxide.

A preferred reaction pressure is about 1 atm.

The reaction is preferably run in a solution with the preferred reaction solvents being DMAC, THF, and DMPU.

The leaving group Y is preferably a bromide, chloride or iodide.

The alkylating agent may preferably be present in the range of about 2.2–4.0 equivalent/amine equivalent to be alkylated. The base catalyst in step (2) is preferably a metal hydride, such as sodium, potassium, or lithium hydride, potassium t-butoxide, potassium hydroxide, sodium hydroxide, potassium carbonate, or sodium carbonate. The process of the present invention may be further understood from Scheme 2.

Scheme 2

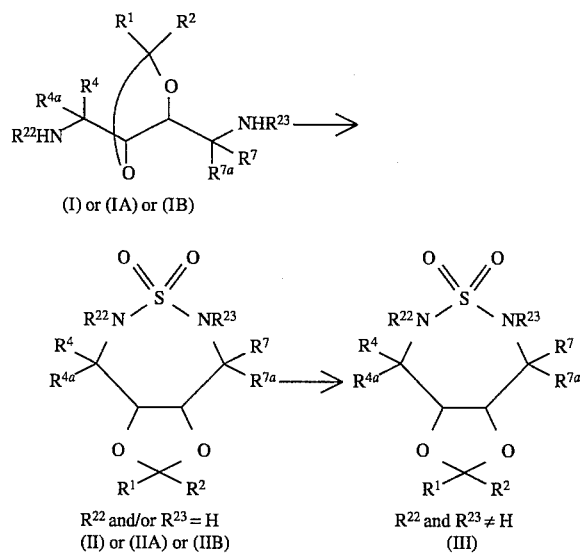

The present invention provides an improved process for the synthesis of compounds of formula (III). Thus, the rate of alkylation was found to be faster and the yield was increased using the acetonide-protected cyclic sulfamide (as in Example 4) than that obtained for the MEM-protected cyclic sulfamide (as in Example 5).

Step 3

The process of the present invention may also comprise the step of deprotection (i.e., removal of the cyclic acetal protecting group) of the compound of formula (III) to form a diol compound of formula (IV). The acetal protecting group may be readily removed under standard conditions known to those skilled in the art. The compounds of formula (IV) are useful as inhibitors of HIV protease for the inhibition of HIV and the treatment of HIV disease.

The compounds of the present invention can be synthesized using the methods described herein, including the representative procedures described in the Examples below. A representative reaction scheme in accordance with the process of the present invention is given below in Scheme 2.

Scheme 2

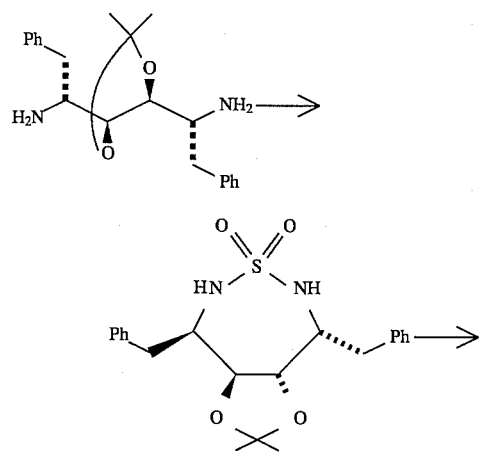

-continued
Scheme 2

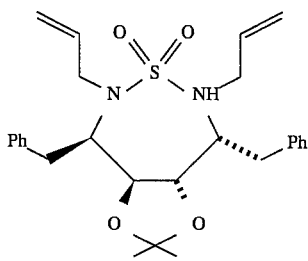

Other representative compounds that can be prepared using the process of the present invention are listed in Table 1.

With a judicious selection of reagents, as is well appreciated to one of skill in the art of organic synthesis, the claimed process can be performed in a straightforward manner to yield the compounds of formula (III) and (IV). The following examples are meant to be illustrative of the present invention. These examples are presented to exemplify the invention and are not to be construed as limiting the invention's scope.

TABLE 1

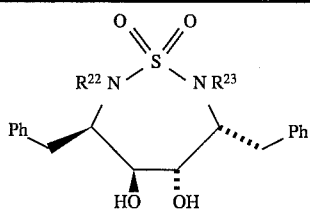

| Ex. No. | $R^{22}$ | $R^{23}$ | MassSpec M + H (M + NH$_4$) |
|---|---|---|---|
| 3 | H | H | 363.1387 |
| 23B | p-(HOCH$_2$)—C$_6$H$_4$CH$_2$— | p-(HOCH$_2$)—C$_6$H$_4$CH$_2$— | 603.2528 |
| 23C | m-(C$_6$H$_5$CH$_2$O)—C$_6$H$_4$CH$_2$— | m-(C$_6$H$_5$CH$_2$O)C$_6$H$_4$CH$_2$— | 755.3155 |
| 23D | m-(HO)—C$_6$H$_4$CH$_2$— | m-(HO)—C$_6$H$_4$CH$_2$— | 575.2216 |
| 23E | allyl | allyl | 443.2005 |
| 23F | cyclopropylmethyl | cyclopropylmethyl | 471.2318 |
| 23G | n-butyl | n-butyl | 475.2631 |
| 23H | beta-naphthylmethyl | beta-naphthylmethyl | 643.2631 |
| 23I | benzyl | benzyl | 543.2306 |
| 23J | p-(C$_6$H$_5$CH$_2$O)—C$_6$H$_4$CH$_2$— | p-(C$_6$H$_5$CH$_2$O)—C$_6$H$_4$CH$_2$— | 755.3147 |
| 23K | p-(HO)—C$_6$H$_4$CH$_2$— | p-(HO)—C$_6$H$_4$CH$_2$— | (592.2486) |
| 23L | m-nitrobenzyl | m-nitrobenzyl | 633.2014 |
| 23M | m-aminobenzyl | m-aminobenzyl | 573.2535 |
| 23N | m-(HOCH$_2$)—C$_6$H$_4$CH$_2$— | m-(HOCH$_2$)—C$_6$H$_4$CH$_2$— | 603.2540 |
| 23O | m-((CH$_3$)$_2$NCH$_2$CO)—C$_6$H$_4$CH$_2$— | m-((CH$_3$)$_2$NCH$_2$CO)—C$_6$H$_4$CH$_2$— | 743.3596 |
| 23P | m-(CH$_3$OCH$_2$)—C$_6$H$_4$CH$_2$— | m-(CH$_3$OCH$_2$)—C$_6$H$_4$CH$_2$— | 631.2832 |
| 23Q | m-(CHO)—C$_6$H$_4$CH$_2$— | m-(CHO)—C$_6$H$_4$CH$_2$— | 599.2211 |
| 23R | CH$_2$-tetrahydro-furan-3-yl | CH$_2$-tetrahydro-furan-3-yl | 531.2533 |
| 23S | m-(HON=CH)—C$_6$H$_4$CH$_2$— | m-(HON=CH)—C$_6$H$_4$CH$_2$— | (646.2708) |
| 23T | m-(CH$_3$CO)—C$_6$H$_4$CH$_2$— | m-(CH$_3$CO)—C$_6$H$_4$CH$_2$— | 627.2523 |
| 23U | m-(HON=C(CH$_3$))—C$_6$H$_4$CH$_2$— | m-(HON=C(CH$_3$))—C$_6$H$_4$CH$_2$— | 657.2739 |
| 23V | CH$_3$ | CH$_3$ | 391.1696 |
| 23W | CH$_2$CH$_3$ | CH$_2$CH$_3$ | 419.2007 |
| 23X | CH$_2$CH$_2$CH$_3$ | CH$_2$CH$_2$CH$_3$ | 447.2316 |
| 23Y | m-(CN)—C$_6$H$_4$CH$_2$— | m-(CN)—C$_6$H$_4$CH$_2$— | 593.2227 |
| 23Z | m-(2-(4-morpholino)-ethylNHC(=O))C$_6$H$_4$CH$_2$— | m-(2-(4-morpholino)-ethylNHC(=O))C$_6$H$_4$CH$_2$— | 855.4111 |
| 23AA | m-(2-(N,N-dimethyl-amino)-ethylNHC(=O))—C$_6$H$_4$CH$_2$— | m-(2-(N,N-dimethyl-amino)-ethylNHC(=O))—C$_6$H$_4$CH$_2$— | 771.3903 |

Each of the references cited herein are hereby incorporated herein by reference.

Example 1

Preparation of Compound of Formula (i)

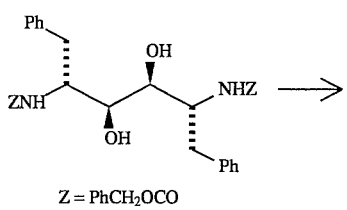

Z = PhCH₂OCO

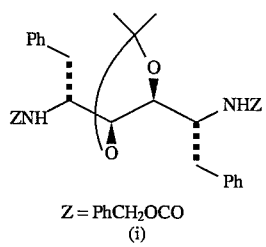

Z = PhCH₂OCO
(i)

In a 5 L four necked flask fitted with a mechanical stirrer was placed 525 g. (0.92 mole) of D-Z-Diol and 2 L of dichloromethane, a thermometer and a reflux condenser with nitrogen bubbler. To it was added 481 g. (4.62 moles) of 2,2-dimethoxypropane and 40 g. (0.17 mole) of camphorsulfonic acid through a powder funnel. The reaction was stirred at room temperature for 18 hrs. At this time a TLC (1/1, ethyl acetate/hexane) showed no starting material present. The reaction was worked up by adding 1L of saturated sodium carbonate to the reaction mixture through an addition funnel, no bubbles. The reaction mixture was transferred to a 5 L separator funnel, washed with 1L of saturated sodium bicarbonate, 1L of distilled water and finally with brine. The methylene chloride solution was dried over sodium sulfate, filtered then evaporated to an orange oil. N = 438 g The oil was dissolved in 500 mL of acetone, not everything went into solution, filtered and washed on the filter with acetone. The acetone was evaporated to another oil which was recrystallized from 300 mL of 1-chlorobutane 1200 mL of hexane. The solution was allowed to stir and crystallize overnight. The white solids were filtered washed on the filter with hexane, dried on the filter then in vacuum. Yield was 372.3 g. 67% Mp=83°–85° C.

Example 2

Preparation of Compound of Formula (I) wherein $R^{22}$, $R^{23}$=H; $R^1$, $R^2$=CH₃; $R^4$; $R^{7a}$=benzyl; $R^{4a}$, $R^7$=H)

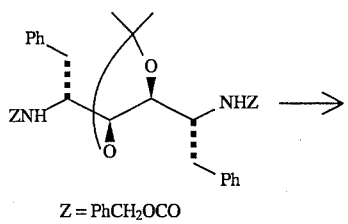

Z = PhCH₂OCO

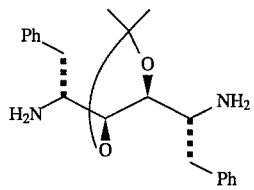

A solution of 75 g (123.3 mmol) of the Cbz-protected compound of formula (I) in 750 mL THF was stirred with a suspension of 7.5 g of 10% Palladium on Carbon under 1 atmosphere hydrogen pressure for 4 hours at room temperature. The mixture was filtered through a celite pad and the pad washed with THF. The filtrate and the washings were concentrated to provide 36 g (86.0%) of intermediate A as an oil. $^{13}$C NMR data was obtained from Varian NMR (75 mHz): (CDCl3) δ27.313, 42.271, 53.768, 80.341, 108.581, 126.247, 128.399, 129.085, 138.870.

Example 3

Preparation of Compound of Formula (II) wherein $R^{22}$, $R^{23}$=H; $R^1$, $R^2$=CH₃; $R^4$; $R^{7a}$=benzyl; $R^{4a}$, $R^7$=H

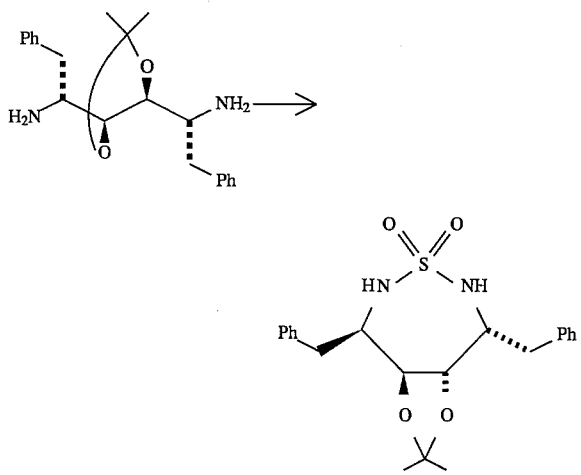

Diamino acetonide compound of the formula (I) 10.0 g (29.5 mmol) and 1,8-diazabicyclo-[5,4,0]undec-7-ene 1 g (6.6 mmol) were dissolved in 100 mL dimethylformamide and to this solution was added 3.12 g (32.5 mmol) sulfamide. The contents were refluxed in a 160° C. oil bath for 1 hour. TLC (1:3 EtOAc:Hexane Rf=0.34) indicated a complete reaction. The reaction was poured slowly into 500 mL water resulting in a thick white slurry. The solid was filtered and washed with water followed by ether. The solid was then triturated with n-butyl chloride, filtered, and washed with hexane. The solid was pumped dry to yield 11.45 g (96.55% yield) of desired cyclized product as a white solid. $^1$H NMR spectra were determined on a Varian spectrometer (300 MHz) δ (DMSO-d₆) 1.429(6H, s), 2.848(2H,m,J=13.545), 3.025(2H,m,J=13.548), 3.694(2H,m), 4.505(2H, s), 6.887 (2H,d), 7.169(4H,m,J=4.394), 7.269(6H,d,J=4.394). C NMR spectra were determined on a Varian spectrometer (75MHz) δ (DMSO-d₆) 27.095, 32,331, 54.035, 76.526, 108.463, 126.130, 128.263, 129.590, 139.467.

Example 4

Preparation of Compound of Formula (III) wherein
R²², R²³=—CH₂CH=CH₂; R¹, R²=CH₃; R⁴,
R⁷ᵃ=benzyl; R⁴ᵃ, R⁷=H

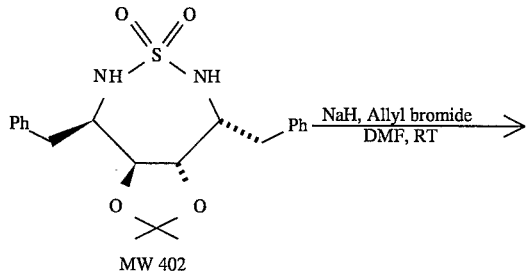

MW 402

NaH, Allyl bromide
DMF, RT

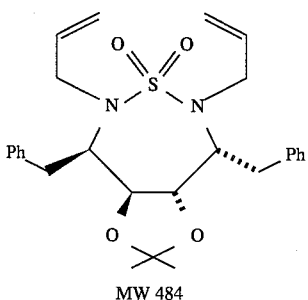

MW 484

In a dry 100 mL Round-Bottom flask was placed 0.81 g (2 mmol) of acetonide protected cyclic sulfamide, 10 mL of DMF. To this magnetically stirred solution was added 0.32 g (8 mmol) of sodium hydride in several portions. There was a vigorous hydrogen evolution. After stirring the reaction mixture for 10 minutes, 0.52 mL (6 mmol) of allyl bromide was slowly added under nitrogen. The solution turned red and the sodium hydride suspension decreased slowly. The reaction mixture was further stirred for 3 hours (TLC showed complete reaction). The reaction mixture was worked up by quenching it carefully with saturated ammonium chloride and the aqueous layer was extracted with 2×25 mL hexane. The combined organic extract was washed with two 25 mL portions of water. The residue after removal of solvent was purified by silica gel column chromatography (1:10 ethyl acetate/hexanes was used for elution) to provide 0.89 g (92% yield) of the desired bisalkylated cyclic sulfamide derivative. Calculated Mass (M+H)=483.231755; FAB Mass Found (M+H)= 483.232495.

Example 5

Bis-alkylation of Di-MEM Protected Cyclic Sulfamide

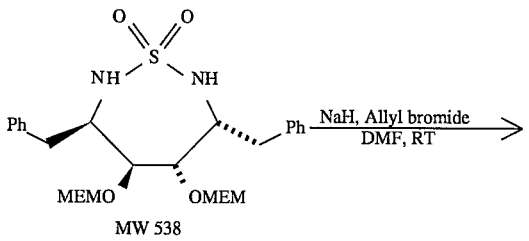

MW 538

NaH, Allyl bromide
DMF, RT

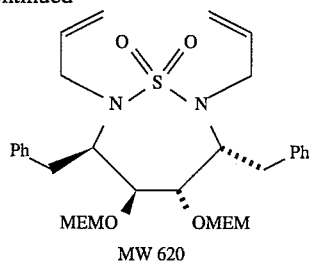

MW 620

In a dry 100 mL round-bottom flask was placed 1.08 g (2 mmol) of di-MEM protected cyclic sulfamide (shown above), 10 mL of DMF. To this magnetically stirred solution was added 0.32 g (8 mmol) of sodium hydride in several portions. The hydrogen evolution was slow. After stirring the reaction mixture for 10 minutes, 0.52 mL (6 mmol) of allyl bromide was slowly added under nitrogen and further stirred for 3 hours (TLC showed incomplete reaction). The reaction mixture was worked up by quenching it carefully with saturated ammonium chloride and the aqueous layer was extracted with 2×25 mL hexane. The combined organic extract was washed with two 25 mL portions of water. The residue after removal of solvent was purified by silica gel column chromatography (1:1, ethyl acetate/hexanes was used for elution) to provide 0.80 g (65% yield) of the desired bisalkylated cyclic sulfamide derivative. Calculated Mass (M+H)=619.305314; FAB Mass Found (M+H)= 619.306759.

The present invention may be embodied in other specific forms without departing from the spirit or essential attributes thereof and, accordingly, reference should be made to the appended claims as further indicating the scope of the invention.

What is claimed is:

1. A process for the preparation of compounds of formula (III)

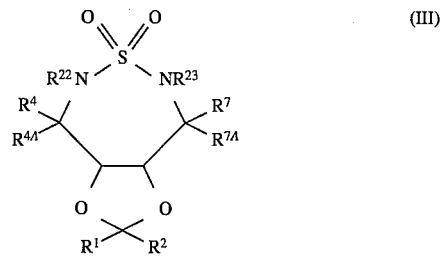

(III)

wherein:

R⁴ and R⁷ are independently selected from the following groups:

hydrogen;

C₁–C₈ alkyl substituted with 0–3 R¹¹;

C₂–C₈ alkenyl substituted with 0–3 R¹¹;

C₂–C₈ alkynyl substituted with 0–3 R¹¹;

a C₃–C₁₄ carbocyclic ring system substituted with 0–3 R¹¹ or R¹²;

a 5- to 10-membered heterocyclic ring system containing 1 to 4 heteroatoms independently selected from oxygen, nitrogen or sulfur, said heterocyclic ring system being substituted with 0–2 R¹²;

—OR¹³; —SR¹³; CO₂R¹³;

R⁴ᴬ and R⁷ᴬ are independently selected from the following groups:

hydrogen;

$C_1$–$C_4$ alkyl substituted with $C_1$–$C_2$ alkoxy;

benzyl substituted with $C_1$–$C_2$ alkoxy;

—$OR^{13}$; —$SR^{13}$; $CO_2R^{13}$;

$R^4$ and $R^{4A}$ can alternatively join to form a 5–7 membered carbocyclic ring substituted with 0–2 $R^{12}$;

$R^7$ and $R^{7A}$ can alternatively join to form a 5–7 membered carbocyclic ring substituted with 0–2 $R^{12}$;

$R^1$ and $R^2$ are independently H, $C_1$–$C_4$ alkyl, $C_1$–$C_4$ alkoxy, $C_6$–$C_{10}$ aryl, $C_7$–$C_{14}$ arylalkyl, $C_3$–$C_7$ cycloalkyl, or, alternately, $R^1$ and $R^2$ can be taken together with the carbon to which they are attached to form a 3–7 membered saturated carbocyclic ring system;

$R^{11}$ is selected from one or more of the following:

H, keto, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl (O-protected), methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;

1–3 amino acids linked together via amide bonds, and said amino acid being linked to $R^4$ or $R^7$ via the amine or carboxylate terminus;

—($C_1$–$C_3$ alkyl)aryl substituted with 0–2 $R^{12}$;

a $C_5$–$C_{14}$ carbocyclic residue substituted with 0–3 $R^{12}$.

a 5- to 10-membered heterocyclic ring system containing 1 to 4 heteroatoms independently selected from oxygen, nitrogen or sulfur, said heterocyclic ring system being substituted with 0–3 $R^{12}$.

$R^{11A}$ is selected from one or more of the following:

H, keto, cyano, —$CH_2NH_2$, —$NH_2$, —$CO_2H$, —$OC(=O)(C_1$–$C_3$ alkyl), —OH, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl (O-protected), methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino) ethoxy, azido, aryl ($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system;

$R^{12}$ when a substituent on carbon, is selected from one or more of the following:

phenyl, benzyl, phenethyl, phenoxy, benzyloxy, O-protected hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, $C_1$–$C_4$ alkyl substituted with , —$NR^{13}R^{14}$, —$NR^{13}R^{14}$, $C_2$–$C_6$ alkoxyalkyl, $C_1$–$C_4$ hydroxyalkyl (O-protected), methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy, O-protected hydroxy, or —$NR^{13}R^{14}$; or, when $R^{12}$ is attached to a saturated carbon atom, it may be =O or =S;

$R^{12}$ when a substituent on nitrogen, is selected from one or more of the following:

phenyl, benzyl, phenethyl, O-protected hydroxy, $C_1$–$C_4$ hydroxyalkyl (O-protected), $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{13}$ is selected from:

phenyl substituted with 0–3 $R^{11A}$;

benzyl substituted with 0–3 $R^{11A}$;

$C_1$–$C_6$ alkyl substituted with 0–3 $R^{11A}$;

$C_2$–$C_4$ alkenyl substituted with 0–3 $R^{11A}$;

$C_1$–$C_6$ alkylcarbonyl substituted with 0–3 $R^{11A}$;

$C_1$–$C_6$ alkoxycarbonyl substituted with 0–3 $R^{11A}$;

$C_1$–$C_6$ alkylaminocarbonyl substituted with 0–3 $R^{11A}$;

$C_3$–$C_6$ alkoxyalkyl substituted with 0–3 $R^{11A}$;

an amine protecting group when $R^{13}$ is bonded to N;

a hydroxy protecting group when $R^{13}$ is bonded to O;

$R^{14}$ is selected from:

$CF_3$;

$C_1$–$C_6$ alkyl substituted with 0–3 groups selected from —O—SEM, $C_1$–$C_4$ alkoxy, —$NHCO_2Bu^t$, —$N(C_1$–$C_4$ alkyl)—$CO_2Bu^t$;

$C_1$–$C_6$ alkoxy;

—NH—$CO_2Bu^t$;

$C_2$–$C_6$ alkenyl;

benzyl;

an amine protecting group when $R^{14}$ is bonded to N;

a hydroxy protecting group when $R^{14}$ is bonded to O;

$R^{13}$ and $R^{14}$ can alternatively join to form $(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

$R^{22}$ and $R^{23}$ are independently selected from the following:

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–2 $R^{32}$;

—$OR^{22a}$; —$N(R^{22a})(R^{22b})$;

31

$R^{22a}$ and $R^{22b}$ are independently selected from the following:

hydrogen;

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ or $R^{32}$; a 5- to 10-membered heterocyclic ring system containing 1 to 4 heteroatoms independently selected from oxygen, nitrogen or sulfur, said heterocyclic ring system being substituted with 0–2 $R^{32}$;

$R^{31}$ is selected from one or more of the following:

ketal, acetal, cyano, —$CH_2NR^{13}R^{14}$, —$NR^{13}R^{14}$, —$CO_2Bu^t$, —$C(=O)R^{11}$, —C $(OR^{22a})_2$—$R^{11}$, —$OR^{13}$, $C_2$–$C_6$ alkoxyalkyl, —$S(O)_mR^{13}$, —$N(SEM)C(=NSEM)N(SEM)R^{13}$, —$C(=NSEM)N(SEM)R^{13}$, —$C(=O)NR^{13}R^{14}$, —$NR^{14}C(=O)R^{13}$, =$NOR^{14}$, —$NR^{14}C(=O)OR^{14}$, —OC$(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, SEM protected oxime, SEM protected sulfonamide, formyl, $C_3$–$C_6$ cycloalkoxy, $C_1$–$C_4$ alkyl substituted with —$NR^{13}R^{14}$, $C_1$–$C_4$ SEM protected hydroxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})=N(OR^{14})$; or 1–3 amino acids, linked together via amide bonds, and said amino acid being linked to $R^{22}$ or $R^{23}$ via the amine or carboxylate terminus;

a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3$–$C_{10}$ cycloalkyl, $C_3$–$C_6$ cycloalkylmethyl, $C_7$–$C_{10}$ arylalkyl, BOC protected hydrazide, benzyl protected oxime, $C_2$–$C_6$ alkoxyalkyl, methylenedioxy, ethylenedioxy, $C_1$–$C_4$ alkylcarbonyloxy, —$NHSO_2R^{14}$, benzyloxy, 2-(1-morpholino) ethoxy, —$CO_2Bu^t$, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —C$(=O)NR^{13}R^{14}$, —$OC(=O)NR^{13}R^{14}$, —$C(=O)R^{11}$, phenyl, —$C(=O)NR^{13}$—($C_1$–$C_4$ alkyl) —$NR^{13}R^{14}$, —$C(=O)NR^{40}R^{41}$, or —$C(=O)NR^{13}C(R^{11})_2NR^{13}R^{14}$; —$C(=O)NR^{13}C(R^{11})_2NR^{13}NR^{14}$;

—$C(=O)NR^{13}C(R^{11})_2NR^{13}CO_2R^{13}$;

—$C(=O)NR^{13}$—($C_1$–$C_4$ alkyl)—$NR^{13}CO_2R^{13}$;

—$C(=O)N(R^{13})$—($C_1$–$C_4$ alkyl)—$R^{11}$; or

—$C(=O)C(R^{11})_2NR^{13}R^{14}$;
—$C(=O)C(R^{11})_2NR^{13}NR^{14}$;

—$C(=O)C(R^{11})_2NR^{13}CO_2R^{13}$; —$C(=O)$—($C_1$–$C_4$ alkyl)—$NR^{13}R^{14}$; —$C(=O)$—($C_1$–$C_4$ alkyl)—$NR^{13}CO_2R^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH;

32

$C_1$–$C_4$ alkyl substituted with 0–4 groups selected from: $R^{11}$, =$NR^{14}$, =$NNR^{13}C(=O)NR^{13}R^{14}$ or —$NR^{13}R^{14}$;

$C_2$–$C_4$ alkenyl substituted with 0–4 $R^{11}$;

$C_2$–$C_4$ alkynyl substituted with 0–4 $R^{11}$;

a 5- or 6-membered heterocyclic ring containing from 1 to 4 heteroatoms independently selected from oxygen, nitrogen or sulfur;

or $R^{32}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, benzyloxy, or —$NR^{13}R^{14}$; or, when $R^{32}$ is attached to a saturated carbon atom, it may be =O, =NObenzyl or =S;

$R^{32}$ when a substituent on nitrogen, is selected from one or more of the following:

phenyl, benzyl, phenethyl, O-protected hydroxy, $C_1$–$C_{14}$ hydroxyalkyl (O-protected), $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{40}$ is selected from: $C_1$–$C_3$ alkyl;

$R^{41}$ is selected from:

—$C(=O)NR^{13}R^{14}$;

—$C(=O)NR^{13}NR^{14}$;

—$C(=O)C(R^{11})_2NR^{13}R^{14}$;

—$C(=O)C(R^{11})_2NR^{13}NR^{14}$;

—$C(=O)C(R^{11})_2NR^{13}CO_2R^{13}$;

—$C(=O)H$;

—$C(=O)R^{11}$;

—$C(=O)$—($C_1$–$C_4$ alkyl)—$NR^{13}R^{14}$;

—$C(=O)$—($C_1$–$C_4$ alkyl)—$NR^{13}CO_2R^{13}$;

1–3 amino acids linked together via amide bonds, and linked to the N atom via the carboxylate terminus;

with the proviso that: $R^4$, $R^{4A}$, $R^7$ and $R^{7A}$ are not all hydrogen;

said process comprising the steps of:

(1) contacting a compound of formula (I) or (IA) (IB):

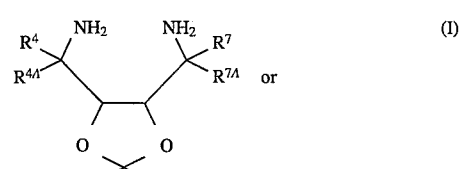
(I)

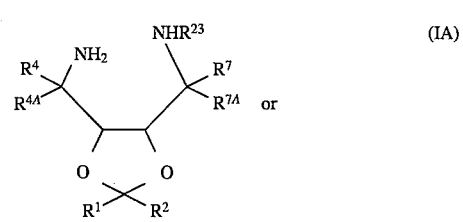
(IA)

-continued

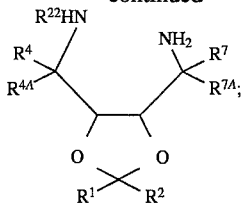

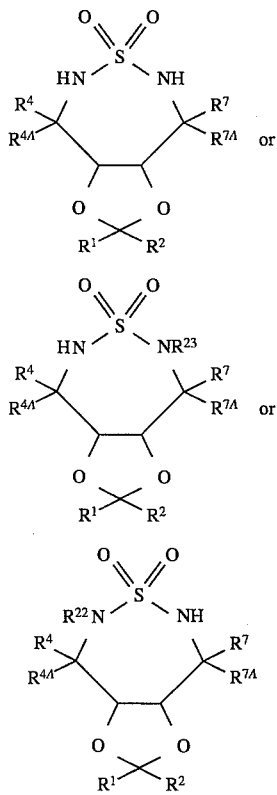

wherein $R^{22}$, $R^{23}$, $R^4$, $R^{4A}$, $R^7$, $R^{7A}$, $R^1$, and $R^2$ are defined above, in a suitable solvent with a hindered amine base and a —S(=O)$_2$— precursor to obtain a compound of the formula (II) or (IIA) or (IIB);

(2) contacting the compound of formula (II) or (IIA) or (IIB) of step (1) above, with a suitable base and an alkylating agent of formula $R^{22}$—Y or $R^{23}$—Y, where Y is a suitable leaving group, to obtain a compound of formula (III).

2. A process of claim 1 wherein:

$R^1$ and $R^2$ are independently H, $C_1$–$C_4$ alkyl, or, alternately, $R^1$ and $R^2$ can be taken together with the carbon to which they are attached to form a 5-6 membered saturated carbocyclic ring system;

$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
$R^{4A}$ and $R^{7A}$ are hydrogen;
$R^{11}$ is selected from one or more of the following:
H, keto, cyano, —CH$_2$NR$^{13}$R$^{14}$, —NR$^{13}$R$^{14}$, —OR$^{13}$, —S(O)$_m$R$^{13}$, $C_1$–$C_4$ alkyl, $C_2$–$C_4$ alkenyl, $C_3$–$C_{10}$ cycloalkyl substituted with 0–2 $R^{12}$, a $C_5$–$C_{14}$ carbocyclic residue substituted with 0–3 $R^{12}$, aryl($C_1$–$C_3$ alkyl)—, substituted with 0–2 $R^{12}$, aryl substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$ when a substituent on carbon, is selected from one or more of the following:
phenyl, benzyl, phenethyl, phenoxy, benzyloxy, O-protected hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —OR$^{13}$, $C_1$–$C_4$ alkyl substituted with —NR$^{13}$R$^{14}$, —NR$^{13}$R$^{14}$, $C_2$–$C_6$ alkoxyalkylene optionally substituted with —Si(CH$_3$)$_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino —S(O)$_m$R$^{13}$, —SO$_2$NR$^{13}$R$^{14}$, —NHSO$_2$R$^{14}$, 2-(1-morpholino)ethoxy, —C(R$^{14}$)=N(OR$^{14}$); or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, O-protected hydroxy, or —NR$^{13}$R$^{14}$; or, when $R^{12}$ is attached to a saturated carbon atom, it may be =O or =S; or when $R^{12}$ is attached to sulfur it may be =O;

$R^{12}$ when a substituent on nitrogen, is selected from one or more of the following:
phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl $C_3$–$C_6$ cycloalkylmethyl, —CH$_2$NR$^{13}$R$^{14}$, —NR$^{13}$R$^{14}$, $C_2$–$C_6$ alkoxyalkyl, $C_1$–$C_4$ alkylcarbonyl, —C(R$^{14}$)=N(OR$^{14}$);

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a hydroxy protecting group when $R^{14}$ is bonded to O;

m is 0, 1 or 2;

$R^{22}$ and $R^{23}$ are independently selected from the group consisting of: hydrogen, allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, benzyl, isoprenyl, propargyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloromethylthienyl, benzyloxybenzyl, phenylbenzyl, adamantylethyl, cyclopropylmethoxybenzyl, methoxybenzyl, methylbenzyl, ethoxybenzyl, benzyloxybenzyl, hydroxymethylbenzyl (with suitable protecting group), aminobenzyl (with suitable protecting group), formylbenzyl, cyanobenzyl, cinnamyl, allyloxybenzyl, fluorobenzyl, difluorobenzyl, chlorobenzyl, iodobenzyl, bromobenzyl, cyclobutylmethyl, formaldoximebenzyl, cyclopentylmethyl, nitrobenzyl, carbo-t-butoxybenzyl, tetrazolylbenzyl, dimethylallyl, 2,5-dimethyl-N-pyrrolylmethylbenzyl, (O-benzylformaldoxime) benzyl, (O-methyl-formaldoxime) benzyl, (benzyl-OCH$_2$CH$_2$N=CH)-benzyl, (CH$_3$)$_3$OCON (CH$_3$)benzyl, (CH$_3$)$_3$OCONbenzyl (CH$_3$)$_3$OCON (CH$_2$CH$_3$)benzyl, (CH$_3$)$_3$OCON (CH$_2$CH$_3$)methlybenzyl, p-(1,1-dimethoxy) ethylbenzyl, N-benzyloxyaminobenzyl, N-benzyloxyethylbenzyl, (CH₃C(=NO-benzyl))-benzyl, (CH₃ONHC (=O))-benzyl, (benzyl-ONHC (=O)) -benzyl, (CH₃NHC(=O)) -benzyl, N,N-dimethylaminocarbonylbenzyl, (benzyl-OCH₂CH(O-benzyl) CH₂O) -benzyl, benzyloxyethoxybenzyl (oxazolidinyl) -benzyl, (benzyloxyl) hexyl, hexenyl, (benzyloxy) octyl, (benzyloxyl) pentyl, (carbo-t-butoxy) pentyl, N, N-dimethylaminomethylbenzyl, (N-phenylmethoxy-carbonyl) alanylaminobenzyl, phenylalanylaminobenzyl, (N-phenylmethoxycarbonyl) phenylalanylaminobenzyl, (CH₃CH₂NHC(=O)) -benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (benzyloxypropynyl)benzyl, (imidazolyl-C(=O))benzyl, (pyrazolyl-C(=O))-benzyl, (pyridylmethylaminocarbonyl)benzyl, (oxadiazolidinonyl)benzyl, trifluoroacetylbenzyl, pyrazolylbenzyl (SEM protected), 1,2-dibenzyloxyethylbenzyl, methanesulfonylpentyl, methoxypentyl, N-formyl-N-methylaminobenzyl, acetylaminobenzyl, propionylbenzyl, butyrylbenzyl, (CH₃CH₂C (=NO-benzyl))-benzyl, (CF₃C(=NO-benzyl))-benzyl, (N-methylglycyl)aminobenzyl, ((4-morpholino)ethyl)aminocarbonylbenzyl, (N,N-dimethylaminoethyl)aminocarbonylbenzyl, (N,N-dimethylaminoethyl)aminocarbonylbenzyl, (4-methylpiperazin-1-ylethyl)aminocarbonylbenzyl, (benzyl—NHC(=O)O)benzyl, (CH₃NHC(=O)O)benzyl, ((N-phenylmethoxycarbonyl)glycylamino)benzyl, (imidazolylmethyl)benzyl, ((CH₃)₃C—C(=O)) benzyl, (N-methyl-N-ethylaminoethyl)aminocarbonylbenzyl, (pyrrolidinylethyl)aminocarbonylbenzyl, (piperidinylethyl)aminocarbonylbenzyl, benzimidazolylmethyl, benzotriazolylmethyl, indazolylmethyl, benzoxazolinylmethyl, benzisoxazolylmethyl, thienylmethyl, or furylmethyl.

3. A process of claim 1 wherein:

$R^1$ and $R^2$ are independently methy, ethyl, or, alternately, $R^1$ and $R^2$ can be taken together with the carbon to which they are attached to form cyclopentyl;

$R^4$ and $R^7$ are independently selected from: benzyl, fluorobenzyl, pyrrolylmethyl, methoxybenzyl, isobutyl, nitrobenzyl, aminobenzyl (with base stable amine protecting group), thienylmethyl, hydroxybenzyl (with base stable hydroxy protecting group), pyridylmethyl, or naphthylmethyl;

$R^{44}$ and $R^{7A}$ are hydrogen;

$R^{22}$ and $R^{23}$ are independently selected from: 4-hydroxy methylbenzyl (with base stable hydroxy protecting group), 3-hydroxybenzyl (with base stable hydroxy protecting group), cyclopropylmethyl, butyl, 2-naphthylmethyl, 4-hydroxybenzyl (with base stable hydroxy protecting group), 3-aminobenzyl (with base stable hydroxy protecting group), 3-hydroxymethylbenzyl (with base stable hydroxy protecting group), 3-((CH₃)₂NCH₂C(=O)NH)-benzyl, 3-(C=NO-benzyl-)benzyl, 3-(CH₃C(=NO-benzyl))-benzyl, m-(3-pyrazolyl)benzyl, P-(3-pyrazolyl)benzyl, benzindazolymethyl, 3-aminobenzindazolymethyl (with base stable N protecting group).

4. A process of claim 1 wherein:

$R^1$ and $R^2$ are methyl;

$R^4$ and $R^7$ are independently selected from: benzyl, fluorobenzyl, pyrrolylmethyl, methoxybenzyl, isobutyl, nitrobenzyl, aminobenzyl (with amino protecting group), thienylmethyl, hydroxybenzyl (with base stable hydroxy protecting group), pyridylmethyl, naphthylmethyl, 4-N, N-dimethylaminobenzyl, 3-N, N-dimethylaminobenzyl, 4-thiazolylmethyl;

$R^{44}$ and $R^{7A}$ are hydrogen;

$R^{22}$ is 5-hydroxypentyl (with base stable hydroxy protecting group) cyclopropylmethyl, butyl, betanaphthylmethyl;

$R^{23}$ is 2-naphthylmethyl, 4-hydroxymethylbenzyl (with base stable hydroxy protecting group), 3-hydroxymethylbenzyl (with base stable hydroxy protecting group), m-(3-pyrazolyl)benzyl, P-(3-pyrazolyl)benzyl, benzindazolymethyl, 3-aminobenzindazolymethyl (with base stable N protecting group).

5. A process of claim 1 wherein step (1) is carried out using one or more of the following conditions: (a) a reaction solvent which is a polar solvent; (b) 0.01–10 molar equivalents of the hindered amine base per molar equivalent of the compound of formula (I), (IA), or (IB); (c) 0.5–3 molar equivalents of a —S(=O)₂— precursor per molar equivalent of the compound of formula (I), (IA), or (IB).

6. A process of claim 1 wherein step (2) is carried out using one or more of the following conditions: (a) a reaction solvent which is an aprotic solvent; (b) 0.5–15 molar equivalents of the suitable base per molar equivalent of the sulfamide amine in the compound of formula (II), (IIA), or (IIB) to be alkylated; (c) 0.5–10 molar equivalents of the alkylating agent per molar equivalent of the sulfamide amine in the compound of formula (II), (IIA), or (IIB) to be alkylated.

7. A process of claim 1 wherein the solvent in step (1) is selected from: dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), tetrahydrofuran (THF), or a hindered amine base.

8. A process of claim 1 wherein the —S(=O)₂ -precursor in step (1) is selected from: sulfamide; SO₂Cl₂; imidazole—S(=O)₂-imidazole; or SOCl₂ followed by oxidation of the cyclic —S(=O)— to —S(=O)₂—.

9. A process of claim 1 wherein the hindered amine base in step (1) is selected from:

aromatic amines, aliphatic amines, alkyl substituted pyridines, 1,8-diazabicyclo[2.2.2]octane, pyridine, 4-pyrrolidinopyridine, 4-piperidinopyridine, N,N-dimethylaminopyridine, trialkyl amines, triethylamine, N,N-diisopropylethylamine, 1,5-diazabicyclo[4.3.0]non-5-ene, 1,8-diazabicyclo[5.4.0]undec-7-ene, or tetramethylethylenediamine.

10. A process of of claim 1 wherein step (1) is carried out under one or more of the following conditions:

the reaction solvent is dimethylformamide, dimethylacetamide, or 1,3-dimethyl-3,4,5,6-tetrahydro-2(1H)-pyrimidinone;

the —S (=O)₂— precursor is sulfamide;

the hindered amine base is present in the range of 0.1–1.0 molar equivalents per mole of the compound of formula (I), (IA), or (B);

the hindered amine base is selected from: 1,8-diazabicyclo[5.4.0]undec-7-ene, 1,8-diazabicyclo[2.2.2]octane, 1,5-diazabicyclo[4.3.0]non-5-ene, or diisopropylethylamine.

11. A process of claim 1 wherein step (2) is carried out in a solvent selected from: dimethylformamide (DMF), dimethylacetamide (DMAC), 1,3-dimethyl-3,4,5,6-tetrahydro-2(1H) -pyrimidinone (DMPU), 1,3-dimethyl-2-imidazolidinone (DMI), N-methylpyrrolidinone (NMP), or tetrahydrofuran (THF).

12. A process of claim 1 wherein the suitable base in step (2) is an alkali metal hydride, alkali metal hydroxide, alkali metal carbonate, or an alkali metal alkoxide.

13. A process claim 1 wherein step (2) is carried out in a solvent selected from: dimethylformamide (DMF), dimethylacetamide (DMAC), 1,3-dimethyl-3,4,5,6-tetrahydro-2(1H)-pyrimidinone (DMPU).

14. A process of claim 1 wherein the suitable base in step (2) is potassium t-butoxide, potassium hydroxide, sodium hydroxide, potassium carbonate, sodium carbonate, sodium hydride, potassium hydride, or lithium hydride.

15. A process of claim 1 further comprising the step of:
(3) treatment of the compound of formula (III) of step (2) under conditions effective to remove the cyclic acetal protecting group, to obtain a compound of formula (IV):

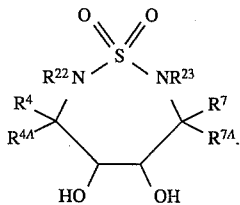
(IV)

16. A process for the preparation of compounds of formula (IV):

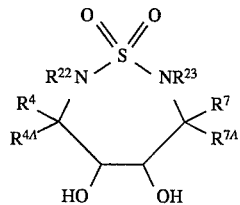
(IV)

wherein:
$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$;
—$OR^{13}$; —$SR^{13}$; $CO_2R^{13}$;
$R^{4A}$ and $R^{7A}$ are independently selected from the following groups:
hydrogen;
$C_1$–$C_4$ alkyl substituted with $C_1$–$C_2$ alkoxy;
benzyl substituted with $C_1$–$C_2$ alkoxy;
—$OR^{13}$; —$SR^{13}$; $CO_2R^{13}$;
$R^4$ and $R^{4A}$ can alternatively join to form a 5–7 membered carbocyclic ring substituted with 0–2 $R^{12}$;
$R^7$ and $R^{7A}$ can alternatively join to form a 5–7 membered carbocyclic ring substituted with 0–2 $R^{12}$;
$R^1$ and $R^2$ are independently H, $C_1$–$C_4$ alkyl, $C_1$–$C_4$ alkoxy, $C_6$–$C_{10}$ aryl, $C_7$–$C_{14}$ arylalkyl, $C_3$–$C_7$ cycloalkyl, or, alternately, $R^1$ and $R^2$ can be taken together with the carbon to which they are attached to form a 3–7 membered saturated carbocyclic ring system;
$R^{11}$ is selected from one or more of the following:
H, keto, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino) ethoxy, azido, or —$C(R^{14})$=$N(OR^{14})$;

1–3 amino acids linked together via amide bonds, and said amino acid being linked to $R^4$ or $R^7$ via the amine or carboxylate terminus;

—($C_1$–$C_3$ alkyl)aryl substituted with 0–2 $R^{12}$;

a $C_5$–$C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:
H, keto, cyano, —$CH_2NH_2$, —$NH_2$, —$CO_2H$, —$OC(=O)$ ($C_1$–$C_3$ alkyl), —$OH$, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl (O-protected), methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino) ethoxy, azido, aryl ($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system;

$R^{12}$ when a substituent on carbon, is selected from one or more of the following:
phenyl, benzyl, phenethyl, phenoxy, benzyloxy, O-protected hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl (O-protected), methylenedioxy, ethylenedioxy, $C_1$–$C_4$ alkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy, —$C(R^{14})$=$N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, O-protected hydroxy, or —$NR^{13}R^{14}$; or, when $R^{12}$ is attached to a saturated carbon atom, it may be =$O$ or =$S$;

$R^{12}$ when a substituent on nitrogen, is selected from one or more of the following:

phenyl, benzyl, phenethyl, O-protected hydroxy, $C_1$–$C_4$ hydroxyalkyl (O-protected), $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl $C_1$–$C_4$ alkoxycarbonyl, —$CO_2H$, $C_1$–$C_4$ alkylcarbonyloxy, $C_1$–$C_4$ alkylcarbonyl, —$C(R^{14})$=$N(OR^{14})$;

$R^{13}$ is selected from:

phenyl substituted with 0–3 $R^{11A}$;

benzyl substituted with 0–3 $R^{11A}$;

$C_1$–$C_6$ alkyl substituted with 0–3 $R^{11A}$;

$C_2$–$C_4$ alkenyl substituted with 0–3 $R^{11A}$;

$C_1$–$C_6$ alkylcarbonyl substituted with 0–3 $R^{11A}$;

$C_1$–$C_6$ alkoxycarbonyl substituted with 0–3 $R^{11A}$;

$C_1$–$C_6$ alkylaminocarbonyl substituted with 0–3 $R^{11A}$;

$C_3$–$C_6$ alkoxyalkyl substituted with 0–3 $R^{11A}$;

an amine protecting group when $R^{13}$ is bonded to N;

a hydroxy protecting group when $R^{13}$ is bonded to O;

$R^{14}$ is selected from:

$CF_3$;

$C_1$–$C_6$ alkyl substituted with 0–3 groups selected from —O—SEM, $C_1$–$C_4$ alkoxy, —$NHCO_2Bu^t$, —$N(C_1$–$C_4$ alkyl)—$CO_2Bu^t$;

$C_1$–$C_6$ alkoxy;

—NH—$CO_2Bu^t$;

$C_2$–$C_6$ alkenyl;

benzyl;

an amine protecting group when $R^{14}$ is bonded to a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

$R^{22}$ and $R^{23}$ are independently selected from the following:

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–2 $R^{32}$;

—$OR^{22a}$; —$N(R^{22a})(R^{22b})$;

$R^{22a}$ and $R^{22b}$ are independently selected from the following:

hydrogen;

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–2 $R^{32}$;

$R^{31}$ is selected from one or more of the following:

ketal, acetal, cyano, —$CH_2NR^{13}R^{14}$, —$NR^{13}R^{14}$, —$CO_2Bu^t$, —$C(=O)R^{11}$, —$C(OR^{22a})_2$—$R^{11}$, —$OR^{13}$, $C_2$–$C_6$ alkoxyalkyl, —$S(O)_mR^{13}$, —$N(SEM)C(=NSEM)N(SEM)R^{13}$, —$C(=NSEM)N(SEM)R^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, SEM protected oxime, SEM protected sulfonamide, formyl, $C_3$–$C_6$ cycloalkoxy, $C_1$–$C_4$ alkyl substituted with —$NR^{13}R^{14}$, $C_1$–$C_4$ protected hydroxyalkyl(O-protected), methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})$=$N(OR^{14})$; or 1-3 amino acids, linked together via amide bonds, and said amino acid being linked to $R^{22}$ or $R^{23}$ via the amine or carboxylate terminus;

a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3$–$C_{10}$ cycloalkyl, $C_3$–$C_6$ cycloalkylmethyl, $C_7$–$C_{10}$ arylalkyl, BOC protected hydrazide, benzyl protected oxime, $C_2$–$C_6$ alkoxyalkyl, methylenedioxy, ethylenedioxy, $C_1$–$C_4$ alkylcarbonyloxy, —$NHSO_2R^{14}$, benzyloxy, 2-(1-morpholino)ethoxy, —$CO_2Bu^t$, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})$=$N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, phenyl, —$C(=O)NR^{13}$—$(C_1$–$C_4$ alkyl)—$NR^{13}R^{14}$, —$C(=O)NR^{40}R^{41}$, or

—$C(=O)NR^{13}C(R^{11})_2NR^{13}R^{14}$;

—$C(=O)NR^{13}C(R^{11})_2NR^{13}NR^{14}$;

—$C(=O)NR^{13}C(R^{11})_2NR^{13}CO_2R^{13}$;

—$C(=O)NR^{13}$—$(C_1$–$C_4$ alkyl)—$NR^{13}CO_2R^{13}$;

—$C(=O)N(R^{13})$—$(C_1$–$C_4$ alkyl)—$R^{11}$; or

—$C(=O)C(R^{11})_2NR^{13}R^{14}$;

—$C(=O)C(R^{11})_2NR^{13}NR^{14}$;

—$C(=O)C(R^{11})_2NR^{13}CO_2R^{13}$; —$C(=O)$—$(C_1$–$C_4$ alkyl)— $NR^{13}R^{14}$; —$C(=O)$—$(C_1$–$C_4$ alkyl)—$NR^{13}CO_2R^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH;

$C_1$–$C_4$ alkyl substituted with 0–4 groups selected from: $R^{11}$, =$NR^{14}$, =$NNR^{13}C(=O)NR^{13}R^{14}$ or —$NR^{13}R^{14}$;

$C_2$–$C_4$ alkenyl substituted with 0–4 $R^{11}$;

$C_2$–$C_4$ alkynyl substituted with 0–4 $R^{11}$;

a 5- or 6-membered heterocyclic ring containing from 1 to 4 heteroatoms independently selected from oxygen, nitrogen or sulfur;

or $R^{32}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, benzyloxy, or —$NR^{13}R^{14}$; or, when $R^{32}$ is attached to a saturated carbon atom, it may be =O, =NObenzyl or =S;

$R^{32}$ when a substituent on nitrogen, is selected from one or more of the following:

phenyl, benzyl, phenethyl, O-protected hydroxy, $C_1$–$C_4$ hydroxyalkyl (O-protected), $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{40}$ is selected from: $C_1$–$C_3$ alkyl;

$R^{41}$ is selected from:
—$C(=O)NR^{13}R^{14}$;
—$C(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$;
—$C(=O)H$;
—$C(=O)R^{11}$;
—$C(=O)$—$(C_1$–$C_4$ alkyl)—$NR^{13}R^{14}$;
—$C(=O)$—$(C_1$–$C_4$ alkyl)—$NR^{13}CO_2R^{13}$;
1–3 amino acids linked together via amide bonds, and linked to the N atom via the carboxylate terminus;

with the proviso that: $R^4$, $R^{4A}$, $R^7$ and $R^{7A}$ are not all hydrogen;

said process comprising the steps of:

(1) contacting a compound of formula (IC):

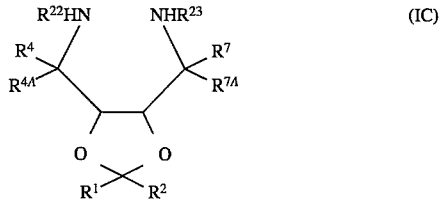

(IC)

wherein $R^{22}$, $R^{23}$, $R^4$, $R^{4A}$, $R^7$, $R^{7A}$, $R^1$, and $R^2$ are defined above, in a solution with a hindered amine base and a —S(=O)$_2$— precursor to obtain a compound of the formula (III):

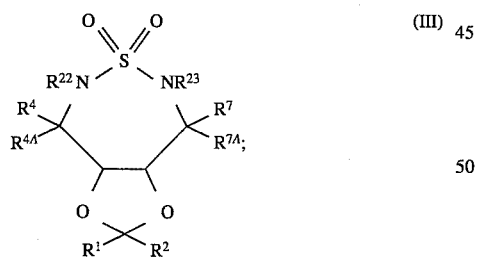

(III)

(2) treatment of the compound of formula (III) of step (1) above under conditions effective to remove the cyclic acetal protecting group, to obtain a compound of formula (IV).

17. A process of claim 16 wherein:

$R^1$ and $R^2$ are independently H, $C_1$–$C_4$ alkyl, or, alternately, $R^1$ and $R^2$ can be taken together with the carbon to which they are attached to form a 5–6 membered saturated carbocyclic ring system;

$R^4$ and $R^7$ are independently selected from the following groups:

hydrogen;

$C_1$–$C_8$ alkyl substituted with 0–3 $R^{11}$;

$C_2$–$C_8$ alkenyl substituted with 0–3 $R^{11}$;

$C_2$–$C_8$ alkynyl substituted with 0–3 $R^{11}$;

$R^{4A}$ and $R^{7A}$ are hydrogen;

$R^{11}$ is selected from one or more of the following:

H, keto, cyano, —$CH_2NR^{13}R^{14}$, —$NR^{13}R^{14}$, —$OR^{13}$, —$S(O)_mR^{13}$, $C_1$–$C_4$ alkyl, $C_2$–$C_4$ alkenyl, $C_3$–$C_{10}$ cycloalkyl substituted with 0-2 $R^{12}$, a $C_5$–$C_{14}$ carbocyclic residue substituted with 0–3 $R^{12}$, aryl($C_1$–$C_3$ alkyl)—, substituted with 0–2 $R^{12}$, aryl substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$ when a substituent on carbon, is selected from one or more of the following:

phenyl, benzyl, phenethyl, phenoxy, benzyloxy, O-protected hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, O-protected hydroxy, or —$NR^{13}R^{14}$; or, when $R^{12}$ is attached to a saturated carbon atom, it may be =O or =S; or when $R^{12}$ is attached to sulfur it may be =O;

$R^{12}$ when a substituent on nitrogen, is selected from one or more of the following:

phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkylcarbonyl, —$C(R^{14})=N(OR^{14})$;

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a O-protected hydroxy protecting group when $R^{14}$ is bonded to O;

m is 0, 1 or 2;

$R^{22}$ and $R^{23}$ are independently selected from the group consisting of: hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloromethylthienyl, benzyloxybenzyl, phenylbenzyl, adamantylethyl, cyclopropylmethoxybenzyl, methoxybenzyl, methylbenzyl, ethoxybenzyl, benzyloxybenzyl, hydroxymethylbenzyl (with suitable protecting group), aminobenzyl (with suitable protecting group), formylbenzyl, cyanobenzyl, cinnamyl, allyloxybenzyl, fluorobenzyl, difluorobenzyl, chlorobenzyl, iodobenzyl, bromobenzyl, cyclobutylmethyl, formaldoximebenzyl, cyclopentylmethyl, nitrobenzyl, carbo-t-butoxybenzyl, tetrazolylbenzyl, dimethylallyl, 2,5-dimethyl-N-pyrrolylmethylbenzyl, (O-benzylformaldoxime) benzyl, (O-methyl-formaldoxime) benzyl, (benzyl-OCH$_2$CH$_2$N=CH)-benzyl, (CH$_3$)$_3$OCON (CH$_3$)benzyl, (CH$_3$)$_3$OCONbenzyl (CH$_3$)$_3$OCON (CH$_2$CH$_3$)benzyl, (CH$_3$)$_3$OCON (CH$_2$CH$_3$)methlybenzyl, p-(1,1-dimethoxy)ethylbenzyl, N-benzyloxyaminobenzyl, N-benzyloxyethylbenzyl, (CH$_3$C(=NO-benzyl))-benzyl, (CH$_3$ONHC(=O)) -benzyl, (benzyl-ONHC(=O)) -benzyl, (CH$_3$NHC(=O)) -benzyl, N,N-dimethylaminocarbonylbenzyl, (benzyl-OCH$_2$CH(O-benzyl)CH$_2$O)-benzyl, benzyloxyethoxybenzyl (oxazolidinyl)-benzyl, (benzyloxyl)hexyl, hexenyl, (benzyloxy)octyl, (benzyloxyl)pentyl, (carbo-t-butoxy) pentyl, N,N-dimethylaminomethylbenzyl, (N-phenylmethoxy-carbonyl)alanylaminobenzyl, phenylalanylaminobenzyl, (N-phenylmethoxycarbonyl) phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (benzyloxypropynyl)benzyl, (imidazolyl-C(=O))benzyl, (pyrazolyl-C(=O))-benzyl, (pyridylmethylaminocarbonyl)benzyl, (oxadiazolidinonyl)benzyl, trifluoroacetylbenzyl, pyrazolylbenzyl (SEM protected), 1,2-dibenzyloxyethylbenzyl, methanesulfonylpentyl, methoxypentyl, N-formyl-N-methylaminobenzyl, acetylaminobenzyl, propionylbenzyl, butyrylbenzyl, (CH$_3$CH$_2$C(=NO-benzyl))-benzyl, (CF$_3$C(=NO-benzyl))benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC (=O)O)benzyl, (CH$_3$NHC(=O)O)benzyl, ((N-phenylmethoxycarbonyl)glycylamino)benzyl, (imidazolylmethyl)benzyl, ((CH$_3$)$_3$C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl, benzimidazolylmethyl, benzotriazolylmethyl, indazolylmethyl, benzoxazolinylmethyl, benzisoxazolylmethyl, thienylmethyl, or furylmethyl.

18. A process of claim 16 wherein:
$R^1$ and $R^2$ are independently methy, ethyl, or, alternately, $R^1$ and $R^2$ can be taken together with the carbon to which they are attached to form cyclopentyl;
$R^4$ and $R^7$ are independently selected from: benzyl, fluorobenzyl, pyrrolylmethyl, methoxybenzyl, isobutyl, nitrobenzyl, aminobenzyl (with base stable amine protecting group), thienylmethyl, hydroxybenzyl (with base stable hydroxy protecting group), pyridylmethyl, or naphthylmethyl;
$R^{4A}$ and $R^{7A}$ are hydrogen;
$R^{22}$ and $R^{23}$ are independently selected from: 4-hydroxy methylbenzyl (with base stable hydroxy protecting group ), 3-hydroxybenzyl (with base stable hydroxy protecting group), cyclopropylmethyl, butyl, 2-naphthylmethyl, 4-hydroxybenzyl (with base stable hydroxy protecting group), 3-aminobenzyl (with base stable hydroxy protecting group), 3-hydroxymethylbenzyl (with base stable hydroxy protecting group), 3-((CH$_3$)$_2$NCH$_2$C(=O) NH)-benzyl, 3-(C=NO-benzyl)benzyl, 3-(CH$_3$C (=NO-benzyl))-benzyl, m-(3-pyrazolyl)benzyl, p-(3-pyrazolyl)benzyl, benzindazolymethyl, 3-aminobenzindazolymethyl (with base stable N protecting group).

19. A process of claim 16 wherein:
$R^1$ and $R^2$ are methyl;
$R^4$ and $R^7$ are independently selected from: benzyl, fluorobenzyl, pyrrolylmethyl, methoxybenzyl, isobutyl, nitrobenzyl, aminobenzyl (with amino protecting group), thienylmethyl, hydroxybenzyl (with base stable hydroxy protecting group), pyridylmethyl, naphthylmethyl, 4-N,N-dimethylaminobenzyl, 3-N,N-dimethylaminobenzyl, 4-thiazolylmethyl;
$R^{4A}$ and $R^{7A}$ are hydrogen;
$R^{22}$ is 5-hydroxypentyl (with base stable hydroxy protecting group) cyclopropylmethyl, butyl, beta-naphthylmethyl;
$R^{23}$ is 2-naphthylmethyl, 4-hydroxymethylbenzyl (with base stable hydroxy protecting group), 3-hydroxymethylbenzyl (with base stable hydroxy protecting group), m-(3-pyrazolyl)benzyl, P-(3-pyrazolyl)benzyl, benzindazolymethyl, 3-aminobenzindazolymethyl (with base stable N protecting group).

20. A process of claim 16 wherein step (1) is carried out using one or more of the following conditions: (a) a reaction solvent which is a polar solvent; (b) 0.01–10 molar equivalents of the hindered amine base per molar equivalent of the compound of formula (IC); (c) 0.5–3 molar equivalents of a —S(=O)$_2$— precursor per molar equivalent of the compound of formula (IC).

21. A process of claim 16 wherein step (2) is carried out using one or more of the following conditions: (a) a reaction solvent which is an aprotic solvent; (b) 0.5–15 molar equivalents of the suitable base per molar equivalent of the sulfamide amine in the compound of formula (IC) to be alkylated; (c) 0.5–10 molar equivalents of the alkylating agent per molar equivalent of the sulfamide amine in the compound of formula (IC) to be alkylated.

22. A process of claim 16 wherein the solvent in step (1) is selected from: dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), tetrahydrofuran (THF), or a hindered amine base.

23. A process of claim 16 wherein the —S(=O)$_2$— precursor in step (1) is selected from: sulfamide; SO$_2$Cl$_2$; imidazole—S(=O)$_2$-imidazole; or SOCl$_2$ followed by oxidation of the cyclic —S(=O)— to —S(=O)$_2$—.

24. A process of claim 16 wherein the hindered amine base in step (1) is selected from:
aromatic amines, aliphatic amines, alkyl substituted pyridines, 1,8-diazabicyclo[2.2.2]octane, pyridine, 4-pyrrolidinopyridine, 4-piperidinopyridine, N,N-dimethylaminopyridine, trialkyl amines, triethylamine, N,N-diisopropylethylamine, 1,5-diazabicyclo[4.3.0] non-5-ene, 1,8-diazabicyclo[5.4.0]undec-7-ene, or tetramethylethylenediamine.

25. A process of of claim 16 wherein step (1) is carried out under one or more of the following conditions:
the reaction solvent is dimethylformamide, dimethylacetamide, or 1,3-dimethyl-3,4,5,6-tetrahydro-2(1H)-pyrimidinone;
the —S(=O)$_2$— precursor is sulfamide;
the hindered amine base is present in the range of 0.1–1.0 molar equivalents per mole of the compound of formula (IC);
the hindered amine base is selected from: 1,8-diazabicyclo[5.4.0]undec-7-ene, 1,8-diazabicyclo[2.2.2]octane, 1,5-diazabicyclo[4.3.0]non-5-ene, or diisopropylethylamine.

* * * * *